(12) United States Patent
Johji et al.

(10) Patent No.: US 7,105,649 B2
(45) Date of Patent: Sep. 12, 2006

(54) GASCI GENE

(75) Inventors: Inazawa Johji, Shinagawa-ku (JP); Imoto Issei, Bunkyo-ku (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 262 days.

(21) Appl. No.: 10/311,002

(22) PCT Filed: Jun. 12, 2001

(86) PCT No.: PCT/JP01/04959

§ 371 (c)(1),
(2), (4) Date: Dec. 12, 2002

(87) PCT Pub. No.: WO01/96566

PCT Pub. Date: Dec. 20, 2001

(65) Prior Publication Data

US 2005/0037345 A1 Feb. 17, 2005

(30) Foreign Application Priority Data

Jun. 12, 2000 (JP) .............................. 2000-174946

(51) Int. Cl.
*C07H 21/04* (2006.01)
(52) U.S. Cl. .................... 536/23.1; 536/23.5; 536/24.3
(58) Field of Classification Search ............... 536/23.1, 536/23.5, 24.3; 435/69.1, 325
See application file for complete search history.

(56) References Cited

U.S. PATENT DOCUMENTS 5,928,884 A * 7/1999 Croce et al. ............... 435/7.23
6,025,480 A * 2/2000 Massague et al. .......... 536/23.1

OTHER PUBLICATIONS

Nagase T., et al. Prediction of the coding sequences of unidentified human genes. XI. The complete sequences of 100 new cDNA clones from brain which code for large proteins in vitro. DNA Res. Oct. 30, 1998;5(5):277-86.*

Accession No.: AB018323 (1999).*
Accession No.: AB037901 (BAB1602;200).*
ID JJ2C-Human.*
Yang ZQ, Imoto I, Fukuda Y, Pimkhaokham A, Shimada Y, Imamura M, Sugano S, Nakamura Y, Inazawa J. Cancer Res. Sep. 1, 2000;60(17):4735-9. Identification of a novel gene, GASC1, within an amplicon at 9p23-24 frequently detected in esophageal cancer cell .*
Nagase, T. et al., "Prediction of the Coding Sequence of Unidentified Human Genes. The Complete Sequences of New cDNA Clones from Braun Which Code for Large Proteins in vitro"., DNA Research, (1998), vol. 5, No. 5, pp. 277-286.
Lock, P. et al., "A new method for isolating tyrosine kinase substrates used to identify Fish, an SH3 and PX domain-containing protein, and Src substrate", The EMBO Journal, (1998), vol. 17, No. 15, pp. 4346-4357.
Yang et al., Identification of a Novel Gene, *GASCI*, within an Amplicon at 9p23-24 Frequently Detected in Esophageal Cancer Cell Lines. *Cancer Res.* 60:4735-4739 (2000).
Database EMBL 'Online!' Feb. 8, 2000, Accession No. AW402136.
Database EMBL 'Online!' Feb. 6, 2000, Accession No. AQ372902.
Database EMBL 'Online!' Feb. 6, 2000, Accession No. AW385519.
Database EMBL 'Online!' May 25, 2000, Accession No. AW887822.

* cited by examiner

*Primary Examiner*—Sheela Huff
*Assistant Examiner*—Lei Yao
(74) *Attorney, Agent, or Firm*—Sughrue Mion, PLLC

(57) ABSTRACT

The invention provides, for example, a gene comprising a polynucleotide coding for the polypeptide having the amino acid sequence shown in SEQ ID NO:3. The gene shows amplification in the 9p23-24 region, has a PX domain and PHD finger motifs, plays an important role in cell growth and differentiation, and in tumorigenesis, and is useful in elucidating the pathology of various diseases caused by a protein involved in cell differentiation in malignant tumor or the like, and in the diagnosis and treatment of such diseases.

6 Claims, 3 Drawing Sheets

GASC1 GENE

TECHNICAL FIELD

The invention relates to a novel gene, more particularly to a novel gene which is located in the region of chromosome p23-24 in human esophagus squamous cells and the amplification and excessive gene product expression of which are observable with malignant alteration of those cells.

BACKGROUND ART

Gene amplification is often observed in tumor cells. Such amplification constitutes one of the mechanisms of protooncogene activation that influences the progress of tumor (Stark, G. R. et al., Cell, 57, 901–908 (1989)). The identification of amplification of a target gene occurring in the amplified region and the characterization of the same provides important information in clarifying the molecular mechanisms of the development and advancement of cancer.

Esophageal carcinoma is ranked as the sixth cause of deaths due to cancers in the world (Pisani, P. et al., Int. J. Cancer, 83, 18–29 (1999)). The two main histopathological types of tumors found in esophageal cancer tissues are squamous cell carcinoma and adenomatous carcinoma. Squamous cell carcinoma is the type most frequently found in Japan as in other countries (Public Welfare White Paper 1999).

Several gene modifications involved in development, advancement and metastasis of esophageal squamous cell carcinoma (inclusive of amplification of MYC, EGFR and CCND1) have already been identified (Lu, S. H. et al., Int. J. Cancer, 42, 502–505 (1988); Jiang, W. et al., Cancer Res., 52, 2980–2983 (1992)).

Recent studies based on the comparative genomic hybridization technique (CGH; Kallioniemi et al., Science, 258, 818–821 (1992)) have newly revealed at least ten amplification regions in esophageal squamous cell carcinoma (Pack, S. D., Genes Chromosomes Cancer, 25, 160–168 (1999); Shinomiya, T. et al., Genes Chromosomes Cancer, 24, 337–344 (1999); Du Plessis, L. et al., Cancer Res., 59, 1877–1883 (1999)). However, no genes involved in esophageal squamous cell cancer have been identified in those detected chromosomal amplification regions.

The inventors searched for abnormal DNA copy numbers in 29 esophageal squamous cell carcinoma cell lines and, as a result, detected several new amplification regions. These amplification regions can be confirmed in the chromosome region 9p23-24 with high frequency.

On the other hand, a genomic change in the chromosome region 9p23-24 is reported to be associated with various malignancies such as nonsmall cell lung carcinoma, liver carcinoma, ovarian carcinoma, uterine cervix carcinoma, mammary carcinoma, osteosarcoma and mediastinal B cell lymphoma (Knuutila, S. et al., Am. J. Pathol., 152, 1107–1123 (1998)).

Taking this report into consideration, it is inferred that there is a possibility that one or more genes capable of functioning as an oncogene activated by amplification might be found in the above chromosome region 9p23-24, irrespective of tissue type.

DISCLOSURE OF INVENTION

The inventors made an intensive study of the chromosome region 9p23-24 including the amplification regions recognized with high frequency in the above-mentioned esophageal squamous cell carcinoma cell lines. Consequently, the inventors succeeded in screening and isolating new tumor-associated genes and transcripts thereof occurring in the 9p23-24 amplification region. One of the genes isolated is a gene (DNA molecule) coding for a protein having the PHD and PX domains (cf. Aasland, R. et al., Trends Biochem. Sci., 20, 56–59 (1995); Lock, P. et al., EMBO J., 17, 4346–4357 (1998)). The inventors named this gene GASC1 (Gene Amplified in Squamous cell Carcinoma 1).

In the present specification, the gene of the invention (DNA molecule) is sometimes referred to as "GASC1 gene", and the protein encoded by the GASC1 gene as "GASC1 protein" and the activity or function of that protein as "GASC1 activity".

The present invention, which has been developed on the basis of the above-mentioned study results, provides the following subject matters (1) to (12):

(1) An isolated DNA molecule comprising one of the following polynucleotides (a) to (d).
  (a) a polynucleotide coding for the poly-peptide consisting of the amino acid sequence shown in SEQ ID NO:3;
  (b) a polynucleotide having at least 95% homology with the nucleotide sequence shown in SEQ ID NO:1;
  (c) a polynucleotide capable of hybridizing with the nucleotide sequence shown in SEQ ID NO:1 under stringent conditions;
  (d) a polynucleotide which is complementary to the above polynucleotide (a) or (b).
(2) An isolated DNA molecule as described above under (1) which is a polynucleotide coding for a polypeptide consisting of the amino acid sequence shown in SEQ ID NO:3.
(3) An isolated DNA molecule as described above under (2) which has the nucleotide sequence shown in SEQ ID NO:1.
(4) An expression product comprising the amino acid sequence shown in SEQ ID NO:3.
(5) A recombinant expression vector comprising the isolated DNA molecule described above under (1) or (3).
(6) A host cell-harboring the recombinant expression vector described above under (5).
(7) which has a sequence comprising at least 30 consecutive nucleotides out of the nucleotide sequence shown in SEQ ID NO:1.
(8) A GASC1 detecting probe as described above under (7) which has a sequence comprising at least 30 consecutive nucleotides out of the nucleotide sequence shown in SEQ ID NO:1.
(9) A cancer diagnostic agent comprising the probe described above under (7) or (8) as an active ingredient.
(10) A cancer diagnostic kit comprising the probe described above under (7) or (8).
(11) An antibody or antibody fragment capable of binding to the expression product of the isolated DNA molecule described above under (1).
(12) A method of diagnosing cancer which comprises the steps of preparing a biological sample, preparing the antibody described above under (11) or a fragment thereof, and immunologically reacting the above sample with the above antibody or fragment and detecting the immune reaction product in the sample.

The present invention also provides the following subject matters (13) to (20):

(13) A cloned cDNA capable of expressing the expression product described above under (4) and an equivalent thereof, for example, a cDNA coding for a modification of the above expression product as derived by deletion, substitution or addition of one or a plurality of amino acid resides in the amino acid sequence of the expression product and having the same activity as the above expression product has and a homologue having a certain level of homology to such cDNAs.

(14) An antisense nucleotide to a sequence comprising at least 15 consecutive nucleotides out of the nucleotide sequence shown in SEQ ID NO:1.

(15) An antisense nucleotide as described above under (14) which is antisense to a sequence comprising at least 30 consecutive nucleotides out of the nucleotide sequence shown in SEQ ID NO:1.

(16) An agent for gene therapy which comprises the antisense nucleotide described above under (14) or (15) as an active ingredient.

(17) (a) A protein comprising the amino acid sequence shown in SEQ ID NO:3 or (b) a protein comprising a modified amino acid sequence derived from the amino acid sequence shown in SEQ ID NO:3 by deletion, substitution or addition of one or a plurality of amino acid residues and being equivalent in activity to the protein comprising the amino acid sequence shown in SEQ ID NO:3.

(18) A method of screening for a substance or substances (agonist and/or antagonist) capable of interacting with the expression product of the isolated DNA molecule described above under (1), the method comprising the steps of cultivating host cells containing the isolated DNA molecule described above under (1) in a medium containing a test substance to be screened, and quantitating the expression product of the isolated DNA molecule described above under (1).

(19) A homologue of the isolated DNA molecule described above under (1) which is isolated from a mammal selected from the group consisting of human, dog, monkey, horse, pig, sheep and cat species.

(20) A therapeutic agent for cancer which comprises an effective amount of the antibody described above under (11) or a fragment thereof together with a pharmaceutically acceptable carrier.

Representation of amino acids, peptides, nucleotide sequences, nucleic acids (nucleotides), etc. by abbreviations in the specification is in conformity with the rules recommended by the IUPAC-IUB, "Guideline for drafting patent specifications etc. relative to nucleotide sequences and/or amino acid sequences" (edited by the Patent Office of Japan) and the conventions relating to the use of codes or symbols in the art.

The inventors performed CGH (comparative genomic hybridization) with 29 esophageal squamous cell carcinoma cell lines and, as a result, confirmed the occurrence of a new tumor-related gene in the chromosome region 9p23-24 in these cell lines.

The inventors also carried out fluorescence in situ hybridization (FISH) and southern blot analysis using YAC (yeast artificial chromosome) and PAC (P1 artificial chromosome) as probes for drawing a gene map for the 9p23-24 amplicon (amplification region).

The inventors further carried out northern blot analysis for screening for a target gene occurring in that amplicon or a transcript thereof. In this way, the inventors succeeded in cloning a novel gene amplified and excessively expressed in several esophageal squamous cell carcinoma cell lines and thus obtained a clone of GASC1 gene.

Upon CGH of esophageal squamous cell carcinoma cell lines (KYSE series) established from surgically excised tumors, the GASC1 gene of the invention showed high levels of amplification in the chromosome region 9p23-24. According to the results of northern blotting, IMAGE clone 131865 (cDNA clone containing a partial sequence of GASC1) alone showed excessive expression in cell lines showing amplification on 9p23-24.

The nucleotide sequence of the GASC1 gene of the invention is determined by the following procedure. Thus, two cDNA libraries are constructed from stomach cancer cell line (HSC39)-derived RNA, the cDNA libraries are screened using the IMAGE clone 131865 as a probe, and the nucleotide sequence of the thus-isolated positive clone is determined.

The GASC1 gene of the invention is specified as a gene having an open reading frame coding for 1,056 amino acid residues shown in SEQ ID NO:3.

The molecular weight calculated for the amino acid sequence encoded by the GASC1 gene of the invention is 120.0 kDa.

According to prior reports, a genetic alteration in the chromosome region 9p is observed in a wide range of human cancers, including esophageal squamous cell carcinoma. According to the results of earlier molecular genetic studies of esophageal squamous cell carcinoma, the region 9p23-24 attracts attention. This region includes, in particular, MTS1 (p16/CDKN2A) coding for an inhibitor of cyclin-dependent kinase 4/6 repressively regulating the G1/S transition stage of proliferating cells (Tanaka, H. et al., Int. J. Cancer, 70, 437–442 (1997)).

Recent studies using CGH and FISH (Inazawa, J. et al., Jpn J. Cancer Res., 83, 1248–1252 (1992)) have revealed that, like in other types of tumor, DNA amplification often occurs in the region 9p23-24 in esophageal squamous cell carcinoma as well (Sonoda, G. et al., Genes Chromosomes Cancer, 20, 320–328 (1997); Taguchi, T. et al., Genes Chromosomes Cancer, 20, 208–212 (1997); Giollant, M. et al., Hum. Genet., 98, 265–270 (1996); Fischer, U. et al., Eur. J. Cancer, 30, 1124–1127 (1994); Sevelyeva, L. et al., Cancer Res., 58, 863–866 (1998)).

Among various reports on the above-mentioned DNA amplification in the region 9p23-24 and related reports, there are the following findings and documentary records, among others.

CGH analysis of human ovarian cancer has revealed that 9p21-pter is one of those sites where an increase in copy number readily occurs. The results of this analysis also indicate that one out of 9 cases showed specific 9p24 amplification and further that the above amplification tends to occur more frequently in the progressive stage of tumor (Sonoda, G. et al., Genes Chromosomes Cancer, 20, 320–328 (1997)).

The 9p23-24 region amplification is also observed in breast cancer, lung cancer, advanced astrocytoma, and glioblastoma (Taguchi, T. et al., Genes Chromosomes Cancer, 20, 208–212 (1997); Giollant, M. et al., Hum. Genet., 98, 265–270 (1996); Fischer, U. et al., Eur. J. Cancer, 30, 1124–1127 (1994); Sevelyeva, L. et al., Cancer Res., 58, 863–866 (1998)).

The breast cancer cell line COLO824 shows an increase in DNA copy number of about 10 times in the 9p23-24 region occurring on the further terminal side of p16/CDKN2A (Sevelyeva, L. et al., Cancer Res., 58, 863–866 (1998)). In addition, redundancy of the 9p23-24 region and a mutation of BRCA2 are reported in three brothers with breast cancer (Sevelyeva, L. et al., Cancer Res., 58, 863–866 (1998)).

Taking these reports into account, it is suggested that the region 9p23-24 is associated with a plurality of tumor types and has at least one tumor-associated gene.

The GASC1 protein has one PX domain and two PHD fingers.

The PX domain occurs in a variety of proteins. This motif may be involved in protein-protein interactions (Lock, P., EMBO J., 17, 4346–4357 (1998)). However, its function has not been fully identified as yet.

The PHD finger, which is one of zinc finger-like sequences, has been widely found in nucleoproteins associated with chromatin-mediated transcriptional regulation, such as the *Drosophila* trl gene product and pc1 gene product (Aasland, R. et al., Trends Biochem. Sci., 20, 56–59 (1995)).

The transcriptional coactivator TIF1 (transcriptional intermediary factor 1), the chromatin-related acetylase MOZ (monocytic leukemia zinc-finger protein) and several PHD finger-containing proteins containing the dermatomyositis-specific autoantigen Mi2 have recently been identified (Venturini, L. et al., 18, 1209–1217 (1999); Borrow, J. et al., Nat. Gene., 14, 33–41 (1996); Zhang, Y., Cell, 95, 279–289 (1998)).

The TIF1 family proteins (α, β, γ) are considered to play an important role in cell differentiation, oncogenesis, and signal transduction (Venturini, L. et al., 18, 1209–1217 (1999)). On the other hand, Mi2 is found in a complex that possesses histone deacetylase and nucleosome-remodeling activities and is involved in chromatin reorganization. The PHD fingers in Mi2 appear to be required for direct interaction of Mi2 with histone deacetylase (Zhang, Y., Cell, 95, 279–289 (1998)).

The PHD motif is also retained in several protooncogenes. HRX/ALL1/MLL (HRX: human trithorax; ALL: acute lymphoblastic leukemia; MLL; mixed lineage leukemia), a human homologue of trx, is frequently altered in acute lymphocytic leukemia in children (Tkachuk, D. C. et al., Cell, 71, 691–700 (1992)) Further, amplification of MLL2, another human homologue of trx, has been observed in tumor cell lines derived from a variety of solid tissues (Huntsman, D. G. et al., Oncogene, 18, 7975–7984 (1999)).

The expression of PLU-1 is consistently observed in breast cancers; however, its expression is highly restricted in normal tissues (Lu, P. et al., J. Biol. Chem., 274, 15633–15645 (1999)).

Mutations within the PHD finger of the AIRE gene have been found in DNA from patients with an autoimmune disease such as APECED (autoimmune polyendocrinopathy-candidiasis-ectodermal dystrophy) (The Finnish-German APECED Consortium. Nat. Genet., 17, 399–403 (1997)).

In a case of acute myeloid leukemia, the MOZ gene was found to be fused with the CBP gene [t(8;16)(p11;p14)] (Borrow, J. et al., Nat. Genet., 14, 33–41 (1996)). Fusion of the RET receptor tyrosine kinase gene with Tif1 has been reported in cases of pediatric papillary thyroid carcinoma (Klugbauer, S., Rabes, H. M., Oncogene, 18, 4388–4393 (1999)).

The GASC1 protein having a deduced amino acid sequence encoded by the GASC1 gene of the invention has two PHD finger motifs. Since the PHD finger motif is found in chromatin-mediated transcriptional region-associated nucleoproteins and a number of protooncogenes, as mentioned above, the GASC1 protein expressed excessively is considered to play an important role in the carcinogenesis and/or progression of various tumors, including esophageal squamous cell carcinoma.

Further, in view of the facts that the PHD motif is found in a number of protooncogenes, that amplification of the 9p23-24 region is often found in esophageal squamous cell carcinoma, that there is a tendency toward the amplification of the 9p23-24 region, in particular, being generally observed in tumors at the progressive stage and, further, that the 9p23-24 region amplification is also observed in breast cancer, lung cancer, advanced astrocytoma and glioblastoma, as mentioned above, the GASC1 gene of the invention which codes for the PHD motif-containing GASC1 protein is considered to play an important role in the development and progression of a plurality of tumors.

Further, as mentioned later herein, the GASC1 protein is associated with squamous cell carcinomas, such as esophageal carcinoma, and, therefore, the gene of the invention supposedly belongs to the group of genes associated with such cancers.

The gene of the invention can regulate the proliferation, differentiation, tumorigenesis, and transcriptional activation, among others, of or in various cells and based on these activities, it can be used in pathology elucidation, diagnosis and treatment, among others, of diseases related to these activities, for example malignant tumor.

The whole or part of the gene of the invention can be used in producing antibodies or fragments thereof, which are capable of binding to the gene expression product (protein). The antibodies or fragments thereof obtained can be used in diagnosing the above-mentioned diseases in which the gene of the invention is involved.

The antisense fragment of the gene of the invention and its expression product can be used in controlling the onset of the above diseases (e.g. tumorigenesis).

The whole or part of the gene of the invention can be used also as a probe. By utilizing the same, it is possible to diagnose cancer and prepare a kit for cancer diagnosis.

Amplification and increased expression of the gene of the invention is observed in tumors and, therefore, the gene of the invention can be used not only in cancer diagnosis but also in judging the malignancy of the cancer.

The gene of the invention can further be used in screening for substances capable of interacting with the GASC1 gene or GASC1 protein.

An example of the gene of the invention is of the human cancer cell origin. By utilizing such gene, it is also possible to obtain homologous genes of various mammals, including human. Further, the use of the gene of the invention makes it possible to identify the gene coding for a protein binding to the protein having the amino acid sequence encoded by the gene of the invention on the C terminal side thereof.

Gene of the Invention

In the following, the gene (DNA molecule) of the invention is described in detail.

In the specification, the term "gene (DNA molecule)" includes not only a double-stranded DNA but also its constituent single-stranded DNA, whether sense or antisense, as well as fragments thereof. Therefore, unless otherwise indicated, the term "gene of the invention" includes a double-stranded DNA containing a human genomic DNA, a single-stranded DNA (sense strand) inclusive of the cDNA, a single-stranded DNA (antisense strand) having a sequence complementary to the sense strand, and fragments thereof.

The gene of the invention may contain a leader sequence, a coding region, exons and introns. The polynucleotide includes both RNA and DNA. The DNA includes cDNA, genomic DNA and synthetic DNA. The polypeptide includes its fragments, homologues, and mutants. The mutants include naturally occurring allele mutants, mutants not existing naturally, mutants having amino acid sequences modified by deletion, substitution, addition and/or insertion, and mutants having functionally equivalent modified amino acid sequences.

A specific example of the gene of the invention is a gene deduced from the DNA sequence which a clone named GASC1 shown later herein in the example section possesses.

The gene (GASC1 gene) incorporated in this clone has an open reading frame (nucleotide sequence shown in SEQ ID NO:1) comprising 3168 nucleotides and coding for the GASC1 protein composed of 1056 amino acid residues as shown in SEQ ID NO:3. From the one-directional cDNA sequence derived from the positive clone, a 4253 nucleotide transcript containing the above 3168 nucleotide single open reading frame was confirmed. The consensus sequence for initiation of translation ("Kozak's rule") is well conserved in that transcript, hence it was confirmed that the initiation codon is at nucleotides Nos. 146–148. The nucleotide sequence of the full-length cDNA in that transcript is as shown in SEQ ID NO:2.

The expression product deduced from the GASC1 gene of the invention contains two PHD finger motifs (residues 687–749 and residues 807–867) on the C terminal side and one PX domain (residues 950–1047).

The gene of the invention includes a DNA molecule having a nucleotide sequence coding for a protein having the amino acid sequence shown in SEQ ID NO:3, and homologues of such DNA molecule.

The above-mentioned homologues are polynucleotides having at least 70% homology, preferably at least 90% homology, more preferably at least 95% homology, most preferably at least 97% homology, with the polynucleotide coding for the polypeptide having the amino acid sequence shown in SEQ ID NO:3 or the polynucleotide having the sequence shown in SEQ ID NO:1.

Such homologous genes include genes having a nucleotide sequence capable of hybridizing with the DNA having a sequence of nucleotides 238–638 out of the sequence shown in SEQ ID NO:1 under stringent conditions, namely in 0.2×SSC containing 0.1% SDS at 50° C. or in 1×SSC containing 0.1% SDS at 60° C.

The DNA molecules having sequence homology to the gene of the invention include a series of related genes recognizable as constituting one gene family based on the commonality or similarity in structural features, gene expression pattern and biological function (including the function of expression product proteins) to the gene of the invention. They, of course, include alleles (allelomorphs) of the GASC1 gene.

Specific examples of the DNA molecules having sequence homology are genes coding for proteins having a certain modification in the amino acid sequence shown in SEQ ID NO:3 and having the same activity as that of the protein having that specified amino acid sequence.

The "certain modification" includes, within the meaning thereof, "deletion, substitution or addition of one or several amino acid sequences or a plurality of amino acid residues". The extent and site(s) of amino acid deletion, substitution or addition are not particularly restricted provided that the modified protein can serve as an equivalent having the same GASC1 activity as the protein (GASC1 protein) having the amino acid sequence shown in SEQ ID NO:3.

The GASC1 activity specifically includes the ability to regulate cell proliferation and differentiation and the ability to regulate tumorigenesis and transcriptional activation.

The amino acid sequence modification (mutation) may occur naturally, for example by spontaneous mutation or posttranslational modification. The modification may also be induced artificially based on the native gene (for example the human GASC1 gene).

The artificial means includes, for example, genetic engineering techniques such as site-specific mutagenesis [Methods in Enzymology, 154, 350, 367–382 (1987); ibid., 100, 468 (1983); Nucleic Acids Res., 12, 9441 (1984); Zoku Seikagaku Jikken Koza (Experiments in Biochemistry, Second Series) 1: "Idenshi Kenkyuho (Methods in Gene Research) II", Japanese Biochemical Society (ed.), p 105 (1986)], methods of chemical synthesis such as the phosphotriester method and phosphoamidite method [J. Am. Chem. Soc., 89, 4801 (1967); ibid., 91, 3350 (1969); Science, 150, 178 (1968); Tetrahedron Lett., 22, 1859 (1981); ibid., 24, 245 (1983)], and combinations of such methods.

More particularly, the DNA can be synthesized by a chemical method such as the phosphoamidite method or phosphotriester method, and this synthesis can be effected on a commercially available automated oligonucleotide synthesizer. The double-stranded fragment can be obtained from the chemically synthesized single-stranded product by synthesizing a complementary strand and annealing the strands under suitable conditions or by adding the complementary strand using a suitable primer sequence together with a DNA polymerase.

The gene of the invention includes any gene coding for a modified or mutated amino acid sequence having GASC1 activity (modified gene), irrespective of the cause and means of such modification/mutation.

The gene coding for such mutated amino acid sequence includes a gene which is silent for amino acid substitution, namely a gene whose nucleotide sequence will not cause any difference in amino acid sequence encoded thereby, and a gene which includes a codon(s) coding for a conservatively substituted amino acid residue(s). The term "conservatively substituted amino acid residue(s)" refers to a substituent amino acid residue(s) other than the original amino acid residue(s) after substitution of which the activity of the polypeptide having the original amino acid residue will still be conserved. Examples of such substituent amino acid residues are shown below, together with the corresponding original amino acid residues.

| Original amino acid residue | Conservatively substituting amino acid residue |
|---|---|
| Ala | Ser |
| Arg | Lys |
| Asn | Gln or His |
| Asp | Glu |
| Cys | Ser |
| Gln | Asn |
| Glu | Asp |
| Gly | Pro |
| His | Asn or Gln |
| Ile | Leu or Val |
| Leu | Ile or Val |

| Original amino acid residue | Conservatively substituting amino acid residue |
| --- | --- |
| Lys | Arg or Glu |
| Met | Leu or Ile |
| Phe | Met, Leu or Tyr |
| Ser | Thr |
| Thr | Ser |
| Trp | Tyr |
| Tyr | Trp or Phe |
| Val | Ile or Leu |

In addition, Cys may be substituted by a different kind of amino acid residue, e.g. Ser, Ala or Val.

In the following cases, for instance, the polypeptide resulting from substitution of an amino acid residue(s) constituting a polypeptide can generally be expected to favorably modify the characteristics thereof.
 a) Substitution of Leu, Ile, Phe, Val or Ala, for instance, for a hydrophilic residue such as Ser or Thr;
 b) Substitution, for Cys or Pro, of any of various other amino acids;
 c) Substitution of an electrically negative amino acid residue, such as Val or Asp, for an amino acid residue having an electrically positive side chain, such as Lys, Arg or His;
 d) Substitution of a side chain-free amino acid residue, such as Gly, for an amino acid residue having a bulky side chain, such as Phe.

The above-mentioned modified amino acid sequences having sequence homology include those amino acid sequences which have a level of identity of at least about 45%, preferably at least about 50%, for the whole amino acid sequence as revealed by searching using the FASTA or BLAST program (Clustal, V., Methods Mol. Biol., 25, 307–318 (1994)). Also included are amino acid sequences showing a level of identity of at least about 35%, preferably at least about 45%, for the PX domain and PHD finger motif domain.

A specific embodiment of the gene of the invention is a gene having the nucleotide sequence shown in SEQ ID NO:1. The coding region in this nucleotide sequence represents an example of the combination of codons for the respective amino acid residues in the amino acid sequence shown in SEQ ID NO:3.

The combination of codons in the gene of the invention is not limited to the one shown in SEQ ID NO:1. Any arbitrary combination of codons can be employed for the respective amino acid residues. Selection of codons can be made in the routine manner. For example, codons can appropriately be selected with reference to the codon usage frequencies in the host to be employed [Nucleic Acids Res., 9, 43 (1981)].

Production of the Gene of the Invention

The gene of the invention can be easily produced and isolated by the general genetic engineering technology based on the sequence information on the gene of the invention as disclosed herein [e.g. Molecular Cloning 2d Ed, Cold Spring Harbor Lab. Press (1989); Zoku Seikagaku Jikken Koza (Experiments in Biochemistry, Second Series): "Idenshi Kenkyuho (Methods in Gene Research) I, II, III, Japanese Biochemical Society (ed.), (1986)].

More particularly, the gene of the invention can be produced by preparing a cDNA library from a suitable source, in which the gene of the invention is expressed, by a routine procedure and selecting a desired clone from that library using a suitable probe or antibody specific to the gene of the invention. Such production procedure can be carried out, for example, according to the method described in the literature [e.g. Proc. Natl. Acad. Sci., USA., 78, 6613 (1981); Science, 222, 778 (1983)].

Appropriate as the source of cDNA are, for example, various cells and tissues expressing the gene of the invention, as well as cultured cells derived therefrom. Isolation of the total RNA from such a source, isolation and purification of mRNA, and acquisition and cloning of cDNA can also be carried out in the conventional manner.

Moreover, commercially available CDNA libraries such as various CDNA libraries available from Clontech Lab. Inc., for instance, can be used in the production of the gene of the invention.

The method of screening for the gene of the invention from a CDNA library is not particularly restricted but the conventional procedure can be employed.

Examples of the screening method include an immunoscreening method using a specific antibody to the protein produced by a cDNA to select the corresponding cDNA clone, a method using a probe selectively binding to the objective DNA sequence, such as a plaque hybridization method or colony hybridization method, and a combination of such methods.

As the probe for the above method, a DNA chemically synthesized according to the nucleotide sequence information on the gene of the invention can be generally employed. The gene of the invention as already obtained or a fragment thereof can also be used as the probe with advantage. Sense primers and antisense primers designed according to the nucleotide sequence information on the gene of the invention can be used as probes for screening.

The nucleotide sequence for use as the probe mentioned above may be a partial nucleotide sequence corresponding to SEQ ID NO:1 and comprising at least 15 consecutive nucleotides, preferably 20 consecutive nucleotides, more preferably 30 consecutive nucleotides, most preferably 50 consecutive nucleotides. Moreover, a positive clone having the sequence shown in SEQ ID NO:1 as such can be used as the probe.

In obtaining the gene of the invention, the DNA/RNA amplification by PCR [Science, 230, 1350 (1985)] can be used with advantage. Particularly when a full-length cDNA can hardly be obtained from a library, the RACE method [Rapid amplification of cDNA ends; Jikken Igaku (Experimental Medicine), 12(6), 35 (1994)], especially the 5'-RACE method [M. A. Frohman, et al., Proc. Natl. Acad. Sci., USA., 8, 8998 (1988)], can be used with advantage.

The primers for use in such PCR methods can be judiciously designed with reference to the sequence information on the gene of the invention as disclosed herein and can be synthesized by the routine procedure. The isolation and purification of the amplified DNA/RNA fragment can be carried out in the routine manner as mentioned above, for example by the gel electrophoresis method.

Sequencing of the gene of the invention or various DNA fragments thereof as obtained in the above manner can be made in accordance with the dideoxy method [Proc. Natl. Acad. Sci., USA., 74, 5463 (1977)] or the Maxam and Gilbert method [Methods in Enzymology, 65, 499 (1980)] or more expediently by using a commercial sequencing kit.

The expression or non-expression of the gene of the invention in an individual or a given tissue can be specifically detected by utilizing a portion or the whole of the nucleotide sequence of the gene of the invention as obtained in the above manner.

The above detection can be made by the conventional procedures, such as RNA amplification by RT-PCR [reverse transcribed-polymerase chain reaction; E. S. Kawasaki, et al., Amplification of RNA. In PCR Protocol, A Guide to Methods and Applications, Academic Press, Inc., SanDiego, 21–27 (1991)]; Northern blot analysis [Molecular Cloning, Cold Spring Harbor Lab. (1989)]; determination on cellular level by in situ RT-PCR [Nucl. Acids Res., 21, 3159–3166 (1993)] or in situ hybridization, for instance; NASBA [nucleic acid sequence-based amplification, Nature, 350, 91–92 (1991)]; etc. The RT-PCR detection method can judiciously be used.

The primers which are to be used when the PCR method is chosen for the above detection may be any ones capable of causing selective amplification of the gene of the invention alone and can be judiciously designed and synthesized based on the sequence information on the gene of the invention. Usually, partial sequences of the gene of the invention, which are about 10–35 nucleotides long, preferably about 15–30 nucleotides long, can be used as the primers.

The gene of the invention, thus, includes the DNA fragments, which can be used as specific primers and/or specific probes for the detection of the gene of the invention.

The DNA fragments mentioned above can be defined as DNAs capable of hybridizing with the DNA having the nucleotide sequence shown in SEQ ID NO:1 under stringent conditions. The stringent conditions mentioned above may be the ordinary conditions under which primers or probes are used. For example, the above-mentioned conditions, namely in 0.2×SSC containing 0.1% SDS at 50° C., or in 1×SSC containing 0.1% SDS at 60° C., may be mentioned.

By utilizing the gene of the invention, it becomes possible to produce the expression product of the gene of the invention (GASC1 protein) or a protein containing the same easily and stably in large quantities by using the conventional genetic engineering techniques.

Protein of the Invention and Production thereof

The invention further provides a protein encoded by the gene of the invention, a vector for the production of the protein, for example a recombinant expression vector containing the gene of the invention, a host cell transformed with the vector, and a method of producing the protein of the invention which comprises cultivating the host cell.

A specific embodiment of the protein of the invention is the GASC1 protein having the amino acid sequence shown in SEQ ID NO:3. The protein of the invention includes any homologue thereof as well. The homologue may be a protein having an amino acid sequence derived from the amino acid sequence shown in SEQ ID NO:3 by deletion, substitution or addition of one or several or a plurality of amino acids and retaining the GASC1 activity. A specific example of the homologue is the expression product of a homologue of the GASC1 gene shown in SEQ ID NO:2 (GASC1 equivalent gene inclusive of its allele)

Furthermore, the homologue of the GASC1 protein of the invention includes proteins having the same activity or function as the GASC1 protein having the amino acid sequence shown in SEQ ID NO:3 as derived from any of human, equine, ovine, bovine, canine, simian, feline, ursine and other mammalian species, and rodents such as rat, mouse and rabbit.

The protein of the invention can be prepared by the conventional recombinant DNA technology [cf. e.g. Science, 224, 1431 (1984); Biochem. Biophys. Res. Comm., 130, 692 (1985); Proc. Natl. Acad. Sci., USA., 80, 5990 (1983)] based on the sequence information on the GASC1 gene as provided by the present invention.

More particularly, the production of the protein is carried out by constructing a recombinant DNA (expression vector) which permits expression of the gene coding for the desired protein in a host cell, transforming the host cell by introducing the vector thereinto, growing the resulting transformant, and harvesting the protein from the culture broth.

The host cell may be whichever of a prokaryotic cell and a eukaryotic cell. Most generally used as the prokaryotic host are *Escherichia coli, Bacillus subtilits* and the like. *Escherichia coli*, in particular strains included among the *Escherichia coli* K12 strain, can be employed with advantage. The eukaryotic host cell includes cells of vertebrates and yeasts, and the former include the simian cell line COS [Cell, 23: 175 (1981)], Chinese hamster ovarian cells, and the dihydrofolate reductase-defective cells thereof [Proc. Natl. Acad. Sci., USA., 77: 4216 (1980)]. The latter include yeast cells of the genus *Saccharomyces*, but these are not exclusive choices.

When prokaryotic cells are used as host cells, an expression plasmid constructed by using a vector replicable in the host cells and adding a promoter and SD (Shine and Dalgarno) sequence upstream of the gene of the invention so that the gene may be expressed therein as well as an initiation codon (e.g. ATG) necessary for initiation of protein synthesis can be used with advantage. As the vector mentioned above, it is usual to employ plasmids derived from *Escherichia coli*, such as pBR322, pBR325, pUC12, pUC13, etc. However, these are not exclusive choices but various known vectors can be utilized. Examples of the commercial vectors for use in expression systems using *E. coli* include pGEX-4T (Amersham Pharmacia Biotech), pMAL-C2, pMA1-P2 (New England Biolabs), pET21, pET21/lacq (Invitrogen) and pBAD/His (Invitrogen).

As the expression vector for use when cells of a vertebrate are used as host cells, the vector to be used generally has a promoter upstream of the gene of the invention to be expressed, RNA splicing sites, a polyadenylation site and a transcription termination sequence. This vector may further have a replication origin where necessary. A specific example of the expression vector is pSV2dhfr having the SV40 early promoter [Mol. Cell. Biol., 1: 854 (1981)]. Aside from the above, various known vectors available commercially can be employed. Examples of the commercial vectors which are used in expression systems using animal cells include vectors for animal cells, such as pEGFP-N, pEGFP-C (Clontech), pIND (Invitrogen), pcDNA3.1/His (Invitrogen), etc., and vectors for insect cells, such as pFastBac HT (Gibco BRL), pAcGHLT (PharMingen), pAc5/V5-His, pMT/V5-His and pMT/Bip/V5-His (all Invitrogen).

pAM82 having a promoter for the acid phosphatase gene [Proc. Natl. Acad. Sci., USA., 80: 1 (1983)] is a specific example of the expression vector for use when yeast cells are used as host cells. The commercial expression vectors for yeast cells include pPICZ (Invitrogen) and pPICZα (Invitrogen).

The promoter is not particularly restricted, either, but any of those known in the art can be utilized. When a strain of the genus *Escherichia* is used as the host, the tryptophan (trp) promoter, lpp promoter, lac promoter, recA promoter, PL/PR promoter, etc. can be utilized with advantage. When the host is a strain of the genus *Bacillus*, the SP01 promoter, SP02 promoter, penP promoter, etc. are preferably used. When a yeast strain is used as the host, the pH05 promoter, PGK promoter, GAP promoter, ADH promoter, etc. can be utilized with advantage. The preferred promoter for use when host cells are animal cells includes the SV40-derived promoters, retrovirus promoters, metallothionein promoter, heat shock promoter, cytomegalovirus promoter, and SRα promoter. These promoters may be used singly or two or more of them may be used combinedly, for example in a connected form.

As the expression vector for the gene of the invention, any conventional fusion protein expression vector can be used with advantage. pGENX (Promega) for the expression of glutathione-S-transferase (GST)-fused proteins is a specific example of such vector.

The method of introducing the desired recombinant DNA (expression vector) into the host cell and the associated transforming method are not particularly restricted but various standardized methods can be utilized.

The transformant obtained can be cultured in the routine manner, whereby the objective protein of the invention is expressed and produced (accumulated/secreted) within cells, outside cells or on the cell membrane of the transformant.

The culture medium to be used for the above cultivation can be judiciously selected from among various routine media according to the kind of adopted host cell, and the culture can also be performed under conditions favoring growth of the host cell.

The thus-obtained recombinant protein of the invention can be optionally isolated and purified by various separation techniques taking advantage of its physical and/or chemical properties, for instance [cf. "Seikagaku Data Book (Biochemical Data Book) II", 1175–1259, First Edition, 1st impression, published Jun. 23, 1980 by Tokyo Kagaku Dozin K.K.; Biochemistry, 25(25), 8274 (1986); Eur. J. Biochem., 163, 313 (1987), etc.].

The above techniques specifically include such conventional methods as reconstitution treatment, treatment with a protein precipitating agent (salting-out method), centrifugation, osmotic shock method, ultrasonic disruption, ultrafiltration, various types of chromatography such as molecular sieve chromatography (gel filtration), adsorption chromatography, ion exchange chromatography, affinity chromatography and high performance liquid chromatography (HPLC), dialysis, and combinations of these. A particularly preferred technique is an affinity chromatography using a column to which a specific antibody to the protein of the invention has been coupled.

In designing the objective gene encoding the protein of the invention, the nucleotide sequence of the GASC1 gene as shown in SEQ ID NO:1 can be utilized with advantage. If desired, this gene can be used after appropriate selection and alteration of the codons specifying the respective amino acid residues. Furthermore, when any amino acid residue or partial sequence of the amino acid sequence encoded by the GASC1 gene is to be modified by substitution, deletion or addition, such modifications can be made by the various methods described above, for example by site-specific mutagenesis.

The protein of the invention can also be produced by the standard protocol for chemical synthesis according to the amino acid sequence shown in SEQ ID NO:3. The method includes the conventional liquid-phase method and solid-phase method for peptide synthesis.

More particularly, the method for peptide synthesis includes the so-called stepwise elongation method in which the constituent amino acids are coupled one by one for chain extension, and the fragment condensation method which comprises synthesizing fragments each consisting of several amino acids beforehand and coupling the fragments together. The protein of the invention can be synthesized by whichever of the above two methods.

The method of condensation for use in the above peptide synthesis may also be a conventional one, including the azide process, mixed acid anhydride process, DCC process, active ester process, redox process, DPPA (diphenylphosphoryl azide) process, DCC+additive (1-hydroxybenzotriazole, N-hydroxysuccinimide, N-hydroxy-5-norbornene-2,3-dicarboximide or the like) process and Woodward's reagent process.

The solvent to be used in these processes can also be judiciously selected from among the common solvents well known in the art for use in such peptide-forming condensation reactions. Examples of the solvents include dimethylformamide (DMF), dimethyl sulfoxide (DMSO), hexamethylphosphoramide, dioxane, tetrahydrofuran (THF), ethyl acetate, etc., and mixtures thereof.

In conducting the peptide synthesizing reactions, the carboxyl group of any amino acid or fragment peptide that should not take part in the reaction can be protected in advance, generally by esterification in the form of a lower alkyl ester such as methyl ester, ethyl ester or tert-butyl ester, or an aralkyl ester such as benzyl ester, p-methoxybenzyl ester, p-nitrobenzyl ester, etc.

Referring to any amino acid having a functional group in its side chain, for example the hydroxyl group of a tyrosine residue, may be protected in advance with an acetyl, benzyl, benzyloxycarbonyl or tertiary butyl group, for instance, although such protection is not necessarily indispensable. Furthermore, the guanidino group of an arginine residue can be protected with a suitable protective group such as nitro, tosyl, p-methoxybenzene-sulfonyl, methylene-2-sulfonyl, benzyloxycarbonyl, isobornyloxycarbonyl, adamantyloxycarboxyl or the like.

The reactions for eliminating such protective groups from the protected amino acids, peptides or the end product protein of the invention can also be carried out in the routine manner, for example by catalytic reduction or by using liquid ammonia/sodium, hydrogen fluoride, hydrogen bromide, hydrogen chloride, trifluoroacetic acid, acetic acid, formic acid, methanesulfonic acid or the like.

The protein of the invention, thus produced, can be purified as needed by the various techniques mentioned above, for example ion exchange resin chromatography, partition chromatography, gel chromatography, countercurrent distribution and like methods in routine use in the field of peptide chemistry.

Antibody Against the Protein of the Invention

The protein of the invention or a fragment thereof can be used with advantage as an immunogen for preparation of specific antibodies thereto. By utilizing this immunogen, the desired antiserum (polyclonal antibody) and monoclonal antibodies can be provided.

The technology of producing antibodies is well known to those skilled in the art and these routine procedures can be employed in practicing the present invention as well [cf. e.g. Zoku Seikagaku Jikken Koza (Experiments in Biochemistry, second series) "Men-eki Seikagaku Kenkyuho (Methods in Immunobiochemistry)", edited by Japanese Biochemical Society (1986)].

The antibody thus obtained can be used with advantage for the purification of the protein of the invention and determination or identification thereof by immunological techniques, among others. More specifically, since amplification and increased expression of the gene of the invention have been confirmed in cancer cells, this antibody can be utilized in cancer diagnosis or cancer malignancy judgment. Furthermore, the above antibody can be used in producing pharmaceutical products comprising the same as an active ingredient, for example diagnostic agents for cancer.

Pharmaceutical Composition of the Invention

The present invention further provides a pharmaceutical composition, for example a therapeutic agent for cancer, which comprises the antibody to the protein of the invention as an active ingredient, or a fragment thereof, as well as a method of producing such composition or agent.

The pharmaceutical composition of the invention is prepared in a form comprising an effective amount of the antibody, or a fragment thereof, to the protein of the invention, together with a pharmaceutically acceptable carrier (inclusive of a diluent).

The carrier which can be used in this pharmaceutical composition (pharmaceutical preparation) can appropriately be selected according to the mode of use of the preparation to be prepared, the unit dosage form thereof, and other factors. It includes, for example, diluents or excipients such as fillers, volume builders, binders, humectants, disintegrates, surfactants, and lubricants.

Most preferably, the pharmaceutical composition of the invention is prepared using various ingredients which can be formulated in ordinary protein preparations, such as a stabilizer, biocide, buffer, isotonizing agent, chelating agent, pH control agent, and surfactant.

The stabilizer includes human serum albumin, ordinary L-amino acids, sugars or saccharides, and cellulose derivatives, for instance. These may be used singly or in combination with a surfactant or the like. The use in combination with a surfactant, in particular, may lead to more effective stabilization of the active ingredient.

The L-amino acid is not particularly restricted but may for example be any of glycine, cysteine and glutamic acid.

The sugar is not particularly restricted but includes monosaccharides such as glucose, mannose, galactose, and fructose; sugar alcohols such as mannitol, inositol, and xylitol; disaccharides such as sucrose, maltose, and lactose; polysaccharides such as dextran, hydroxypropylstarch, chondroitin sulfate, and hyaluronic acid; and their derivatives.

The surfactant is not particularly restricted, either, but both ionic and nonionic surfactants can be employed. Specific examples are polyoxyethylene glycol sorbitan alkyl esters, polyoxyethylene alkyl ethers, sorbitan monoacyl esters, and fatty acid glycerides.

The cellulose derivative that can be used is not particularly restricted, either, but includes methylcellulose, ethylcellulose, hydroxyethylcellulose, hydroxypropylcellulose, hydroxypropylmethylcellulose, and carboxymethylcellulose sodium.

The level of addition of the sugars is not less than about 0.0001 mg, preferably within the range of about 0.01 to about 10 mg, per microgram (pg) of the active ingredient. The level of addition of the surfactant is not less than about 0.00001 mg, preferably within the range of about 0.0001 to about 0.01 mg, per pg of the active ingredient. The level of addition of human serum albumin is not less than about 0.0001 mg, preferably within the range of about 0.001 to about 0.1 mg, per μg of the active ingredient. The amino acid is used in an amount within the range of about 0.001 to about 10 mg per μg of the active ingredient. The level of addition of the cellulose derivative is not less than about 0.00001 mg, preferably within the range of about 0.001 to about 0.1 mg, per μg of the active ingredient.

The amount of the active ingredient in the pharmaceutical preparation of the invention can be liberally selected from a broad range. Generally, it is within the range of about 0.00001 to about 70% by weight, preferably about 0.0001 to about 5% by weight, based on the weight of the pharmaceutical preparation.

The pharmaceutical composition of the invention may be further supplemented with various additives such as a buffer, an isotonizing agent, and a chelating agent. The buffer includes boric acid, phosphoric acid, acetic acid, citric acid, ε-aminocaproic acid, glutamic acid, and/or the corresponding salts (alkali metal or alkaline earth metal salts thereof, such as sodium salts, potassium salts, calcium salts and magnesium salts). The isotonizing agent includes sodium chloride, potassium chloride, sugars, and glycerol, among others. The chelating agent includes sodium edetate and citric acid, among others.

The pharmaceutical preparation of the invention can be used in the form of a solution, or in a lyophilized form derived therefrom, which can be stored. Such lyophilized preparation can be extemporaneously dissolved in, for example, a buffer inclusive of water, physiological saline or the like, to an appropriate concentration for administration.

The amount of the active ingredient to be contained in the pharmaceutical preparation and the dosage thereof are not particularly restricted but can be selected from within a broad range according to the expected therapeutic effect, administration method, duration of treatment, patient background such as age and sex, and other factors. Generally, the recommended usual dosage of the active ingredient is about 0.01 μg to about 10 mg/day, preferably about 0.1 μg to about 1 mg/day, per kg body weight. The preparation may be administered once a day or in 2 to several divided doses.

Antisense Oligonucleotide and Vector for Gene Therapy

The present invention further provides an antisense medicine capable of producing an RNA having a sequence complementary to mRNA within cells to thereby inhibit translation and suppress the expression of the GASC1 gene in cells capable of expressing the GASC1 gene, and a method of gene therapy for cancer which utilizes the same.

The basic principle of the therapy consists in inhibiting the expression of the target GASC1 gene. This expression inhibition is effected, for example, by producing an antisense nucleotide complementary to the mRNA corresponding to the target gene and feeding the same to cancer cells having the target GASC1 gene. The antisense nucleotide binds to the mRNA corresponding to the GASC1 gene in the target cells provided with the nucleotide or is intercalated in the DNA double helix in the target cells to form a triple strand. The process of transcription or translation of the GASC1 gene is thereby inhibited. Through the inhibition of the expression function of the GASC1 gene, the proliferation of a neoplasm or tumor in the receptor cells/target cells can be inhibited.

The antisense nucleotide can be fed to the target cells by introducing a vector or plasmid containing the nucleotide extrachromosomally into the target cells and retaining the same therein. More particularly, the antisense nucleotide is inserted into a vector derived from a retrovirus, adenovirus or AAV, and the target cancer cells are infected with the resulting vector, whereby the antisense nucleotide is fed to the target cells. In the infected cells, the antisense nucleotide is expressed excessively to produce the desired antitumor effect.

In the gene therapy comprising introducing the antisense nucleotide into cells having the GASC1 gene to inhibit the expression of the GASC1 protein, it is not necessary for the antisense nucleotide to have a sequence corresponding to the full length of the GASC1 gene. It may have a sequence corresponding to the gene coding for some or other modification mentioned above or a sequence comprising a part of the GASC1 gene, provided that the same function as the GASC1 gene expression inhibiting function is retained.

Starting or source vectors which can be used for introducing a desired gene thereinto for both introduction thereof into target cells and extrachromosomal maintenance thereof are already known in the relevant field of art. Any of such known starting vectors can be used in the practice of the invention. Suitable starting vectors are, for example, the vectors disclosed in U.S. Pat. No. 5,252,479 and PCT International laid-open specification WO 93/07282 (pWP-7A, pWP-19, pWU-1, pWP-8A, pWP-21, pRSVL, etc.) or the commercial vector pRC/CMV (Invitrogen). Various viral vectors described later herein also are preferred vectors.

The introduction of the desired gene into these starting vectors can be carried out in the routine manner. Vectors or plasmids (introducing vector) for feeding the desired gene to target cells can be obtained by such introduction. These are viral vectors or plasmid vectors containing a copy of the antisense nucleotide to the GASC1 gene as connected to an expression regulating element and being capable of producing the antisense nucleotide product in the target cells. The expression vector containing the gene of the invention as described hereinabove can also be used as an introducing vector.

As the promoter sequences for use in the introducing vector for gene therapy, those promoters, which are intrinsic to the affected tissues to be treated in various diseases, can preferably be employed.

Specific examples thereof are the promoter sequences for albumin, α-fetoprotein, α1-antitrypsin, transferrin, and transthyretin, for the liver, for instance.

For the colon, the promoter sequences for carbonic anhydrase and carcinoembryonic antigen can be mentioned as examples.

For the uterus and placenta, the promoter sequences for estrogen, aromatase, cytochrome P450, cholesterol side-chain-cleaving enzyme P450, and 17α-hydroxylase P450 can be mentioned as examples.

For the prostate, the promoter sequences for prostate antigens, gp91-fox gene, and prostate-specific kallikrein can be mentioned as examples.

For the breast, the promoter sequences for erb-B2, erb-B3, β-casein, β-lactoglobin, and whey protein can be mentioned, as examples.

For the lung, the promoter sequences for surfactant protein C, and uroglobulin can be mentioned as examples.

For the skin, the promoter sequences for K-14-keratin, human keratin 1 or 6, and leucline can be mentioned as examples.

For the brain, the promoter sequences for glial fibrillary acidic protein, mature astrocyte-specific protein, myelin basic protein, and tyrosine hydroxylase can be mentioned as examples.

For the pancreas, the promoter sequences for villin, glucagon, and Langerhans islet amyloid polypeptide can be mentioned as examples.

For the thyroid, the promoter sequences for thyroglobulin and calcitonin can be mentioned as examples.

For the bone, the promoter sequences for α1 collagen, osteocalcin, and bone sialoglycoprotein can be mentioned as examples.

For the kidney, the promoter sequences for renin, liver/bone/kidney alkaline phosphatase, and erythropoietin can be mentioned as examples.

For the pancreas, the promoter sequences for amylase and PAP1 can be mentioned as examples.

Furthermore, the antisense nucleotide to be used in introducing vector production (the whole or a part of the complementary sequence corresponding to the sequence of the GASC1 gene) can be easily produced and acquired by the standard genetic engineering techniques based on the nucleotide sequence information on the GASC1 gene of the invention, as described hereinbefore.

The transfer of such an introduction vector into cells can be carried out by various techniques already known in the art for introducing DNA into cells. Examples thereof are electroporation, calcium phosphate coprecipitation, virus transduction and the like.

The cells transformed or transfected with the antisense nucleotide to the GASC1 gene as a result of transfer of the introducing vector, as such in an isolated state, can also be utilized as model systems for use in research and development of pharmaceuticals and therapeutic research models for the suppression of cancer or prevention of cancer metastasis.

In gene therapy, the above introducing vector can be introduced into patient's tumor cells by injecting the same either topically into the tumor site or sites of the patient or systemically. When systemically administered on that occasion, it can be caused to arrive at all tumor cells, inclusive of metastatic ones possibly occurring at another site or other sites. Generally, the transduced gene is permanently taken up in the chromosome of each target tumor cell upon administration in the above manner. In the event of this being insufficient, the uptake of the desired gene can be secured by repeating the administration periodically.

Gene Therapy

The method for gene therapy according to the invention includes both the in vivo technique which comprises administering a material for introduction of the above antisense nucleotide (antisense nucleotide introducing vector) directly into the body and the ex vivo technique which comprises excising some target cells from the patient's body, extracorporeally transferring the gene thereinto and, then, returning the cells into the body.

The method for gene therapy according to the invention also includes a gene therapy method which comprises introducing the antisense nucleotide to the GASC1 gene directly into cells and utilizing ribozymes, which are active molecules slicing RNA chains.

The agent for gene therapy according to the invention comprises, as an active ingredient, either a gene introducing vector containing the whole or a part of the antisense nucleotide corresponding to the gene of the invention or cells bearing the antisense nucleotide to the gene of the invention as introduced by means of said vector.

The agent for gene therapy according to the invention is primarily indicated in cancer cases, although it can also be used in the therapy (treatment) of other hereditary diseases, for example viral diseases such as AIDS. The agent for gene therapy according to the invention can further be used for the purpose of labeling genes.

In the gene therapy according to the invention, the target cells into which the antisense nucleotide is to be introduced can be judiciously selected according to the object of the gene therapy (treatment). The target cells include not only cancer cells or tumor tissues but also lymphocytes, fibroblasts, hepatocytes and hemopoietic cells, among others.

The method of introducing the antisense nucleotide in the above gene therapy includes a viral introduction technique and a non-viral introduction technique.

As to the viral introduction technique, in consideration of the fact that the antisense nucleotide to the GASC1 gene is a foreign substance which is expressed in normal cells, the method using a retrovirus vector, for instance, can be mentioned. Other viral vectors can also be used and include the adenovirus vector, HIV (human immunodeficiency virus) vector, adeno-associated virus (AAV) vector, herpes virus vector, herpes simplex virus (HSV) vector, and Epstein-Barr virus (EBV) vector, among others.

The non-viral introduction method includes the following methods.

Calcium phosphate coprecipitation method;

Membrane fusion liposome method; the method comprising preparing membrane fusion liposomes by fusing DNA-including liposomes with inactivated Sendai virus prepared by disrupting the genes with ultraviolet rays, directly fusing the liposomes with the cell membrane, and introducing the fusion product into cells [Kato, K. et al., J. Biol. Chem., 266, 22071–22074 (1991)];

Method comprising coating a plasmid DNA with gold and physically introducing the DNA into cells by means of high voltage discharge [Yang, N. S. et al., Proc. Natl. Acad. Sci., 87, 9568–9572 (1990)];

Naked DNA method; the method comprising injecting a plasmid DNA directly into an organ or tumor in vivo [Wolff, J. A. et al., Science, 247, 1465–1467 (1990)];

Cationic liposome method; the method comprising introducing a gene embedded in positively charged multilamellar liposomes into cells [Yagi, Kunio, Igaku no Ayumi (Advances in Medicine), Vol. 175, No. 9, 635–637 (1995)];

Ligand-DNA complex method; the method comprising binding DNA to a ligand binding to a receptor expressed in target cells and administering the binding product so that the gene can be introduced into specific cells alone but may not be introduced into other cells [Frindeis et al., Trends Biotechnol., 11, 202 (1993); Miller et al., FASEB J., 9, 190 (1995)].

The above-mentioned ligand-DNA complex method includes the method comprising using a sialoglycoprotein as the ligand with the sialoglycoprotein receptor expressed in hepatocytes, for instance, as the target [Wu et al., J. Biol. Chem., 266, 14338 (1991); Ferkol et al., FASEB J., 7, 1081–1091 (1993), and the method comprising using transferring as the ligand with the transferrin receptor strongly expressed by tumor cells as the target [Wagner et al., Proc. Natl. Acad. Sci., USA, 87, 3410 (1990)], among others.

The gene introduction or transfer method may consist in an appropriate combination of one or more biological and/or one or more physical gene transfer methods such as mentioned above. In an example of such combination, a plasmid DNA having a certain size is combined with a polylysine-conjugated antibody specific to the adenovirus hexon protein. According to this method, the antibody complex is coupled to the adenovirus vector and, thus, it becomes possible to carry out antisense nucleotide introduction by infecting cells with the thus-obtained trimolecular complex. This method enables efficient binding, integration and endosome decomposition before the DNA coupled to the adenovirus vector is damaged.

Viral Vector Construction and Gene Transfer Method

The method of constructing a viral vector for antisense nucleotide transfer and the method for transfer of the antisense nucleotide to target cells or a target tissue are now specifically described.

The retrovirus vector system consists of a viral vector and a helper cell (packaging cell). The helper cell means a cell which has expressed beforehand genes encoding the structural protein gag (structural protein within the virus particle), pol (reverse transcriptase), env (coat protein), etc. of a retrovirus but which has not formed virus particles. On the other hand, the viral vector has the packaging signal and LTR (long terminal repeats) but lacks structural genes, such as gag, pol, env, etc., which are necessary for virus replication. The packaging signal is a sequence which functions as a tag in the assembly of a virus particle. Selective genes (neo, hyg) and the object antisense nucleotide (whole or a fragment of the antisense nucleotide to the GASC1 gene) ligated in a cloning site are inserted in lieu of the virus genes. In order that a high titer of virus particles may be obtained, it is important to use an insert as short as possible, provide a broad packaging signal including a part of the gag gene, and use care not to leave ATG of the gag gene.

As the vector DNA harboring the object antisense nucleotide to the GASC1 gene is transferred to the helper cell, the vector genomic RNA is packaged by the virus structural protein formed by the helper cell, whereby virus particles are formed and secreted. The virus particle as a recombinant virus infects the target cell and, as a result, the DNA sequence reverse-transcribed from the virus genomic RNA is integrated into the cell nucleus, so that the antisense gene inserted in the vector is expressed.

There may also be employed a technique using a fibronectin fragment containing the cell adhesion domain, heparin-binding site and conjugating segment [Hanenberg, H. et al., Exp. Hemat., 23, 747 (1995)], for enhancing the efficiency of transfer of the object gene.

An example of the retrovirus vector for use in the above retrovirus vector system is the retrovirus derived from mouse leukemia virus (McLachlin, J. R. et al., Proc. Natl. Acad. Res. Molec. Biol., 38, 91–135 (1990)].

The method using an adenovirus vector is now described in detail. The adenovirus vector can be constructed in accordance with the methods described by Berkner [Berkner, K. L., Curr. Topics Microbiol. Immunol., 158, 39–66 (1992)], Yasuhiro Setoguchi et al. [Setoguchi, Y. et al., Blood, 84, 2946–2953 (1994)], Hiromi Kanegae et al. [Kanegae, H. et al., Jikken Igaku (Experimental Medicine), 12, 28–34 (1994)] and Ketner et al. [Ketner, G. et al., Proc. Natl. Acad. Sci., USA., 91, 6186–6190 (1994)].

A non-proliferative adenovirus vector can be constructed in the following manner. Thus, the early gene region E1 and/or E3 of the adenovirus is excised in the first place. Then, a plasmid vector containing the desired foreign gene expression unit (which consists of the antisense nucleotide to be transferred, namely the antisense nucleotide to the GASC1 gene, the promoter for transcription of said antisense nucleotide, Poly A for insuring the stability of the transcribed gene) and a part of the adenovirus genomic DNA and a plasmid containing the adenovirus genome are used to cotransfect the 293 cell, for instance. As a homologous recombination is thus caused to take place between them for substitution of the gene expression unit for El, a nonproliferative adenovirus vector is obtained as a vector harboring the object antisense nucleotide to the GASC1 gene and suited for use in gene therapy according to the invention. A 3'-end adenovirus vector with a terminal protein added can also be constructed by ligating the adenovirus genomic DNA in a cosmid vector. Furthermore, the YAC vector may also be utilized for recombinant adenovirus vector construction.

Production of an adeno-associated virus (AAV) vector is now described briefly. AAV was discovered as a small virus contaminating adenovirus culture systems. As to this virus, the existence of the genus *Parvovirus* capable of autonomous proliferation within the host cell without requiring a helper virus for virus replication and the genus *Dependovirus* which requires a helper virus has been identified. This AAV has a broad host range and is one of the common viruses infecting various kinds of cells. The virus genome is a linear single-stranded DNA consisting of 4680 nucleotides, with the 145 nucleotides at both ends having a characteristic sequence known as ITR (inverted terminal repeat). This ITR region functions as the replication origin and plays the role of a primer. This ITR is also essential to packaging for virus particles and integration of AAV into the chromosomal DNA of the host cell. In regard of the virus protein, the left-half of the genome codes for the nonstructural protein, that is the regulatory protein Rep which controls replication and transcription.

Construction of the recombinant AAV can be carried out by utilizing the property of AAV to become integrated into the chromosomal DNA, whereby the desired gene transfer vector can be prepared. More particularly, this method comprises first constructing a plasmid (AAV vector plasmid) retaining the ITRs at both the 5'- and 3'-ends of a wild-type AVV and harboring the antisense nucleotide (GASC1 antisense nucleotide) to be transferred as interposed therebetween. On the other hand, the virus protein necessary for virus replication and formation of virus particles is supplied from a separate helper plasmid. It is necessary to insure that no common nucleotide sequence will exist between the two plasmids so that a wild-type virus will not appear on DNA recombination. Thereafter, the two plasmids are transferred, by transfection, into the 293 cell, for example, and, further, the cells are infected with an adenovirus as the helper virus (when the 293 cell is used, this adenovirus may be a non-proliferative one), whereby the desired non-proliferative recombinant AAV is produced. Since this recombinant AAV is present in the nucleus, the cells are then subjected to freeze-thawing and recovered and the contaminant adenovirus is inactivated by heating at 56° C. Further, where necessary, the recombinant AAV is separated and concentrated by ultracentrifugation using cesium chloride. In this manner, the desired recombinant AAV for gene transfer can be obtained.

Production of an EBV vector can be carried out by the method of Shimidzu et al. [Shimidzu, N. et al., Saibo Kogaku (Cell Technology), 14(3), 280–287 (1995)], for instance.

Production of the EBV vector for transfer of the antisense nucleotide is now described briefly.

EB virus (Epstein-Barr virus: EBV) is a virus of the family Herpesviridae, which was first isolated by Epstein and coworkers from cultured cells derived from Burkitt lymphoma [Kieff, E. and Liebowitz, D.: Virology, 2nd ed. Raven Press, New York, 1990, pp. 1889–1920]. This EBV has cell-transforming activity and, in order to use it as a vector for gene transfer, it is necessary to prepare a virus lacking this transforming activity. This can be done as follows.

Thus, first of all, the EBV genome in the vicinity of the target DNA in which the desired foreign gene is to be inserted is cloned. Then, a DNA fragment of the foreign gene and a drug-resistant gene are inserted therein to construct a vector for preparation of a recombinant virus. Then, the vector for recombinant virus construction as excised with a suitable restriction enzyme is transfected into EBV-positive Akata cells. The recombinant virus formed by homologous recombination is recovered, together with the wild type Akata EBV, through stimulation of virus production by anti-surface immunoglobulin treatment. The recombinant virus is infected into EBV-negative Akata cells, and drug-resistant clones are selected in the presence of a drug, whereby Akata cells infected exclusively with the recombinant virus free of wild type EBV can be obtained. Further, by inducing viral activity in the recombinant virus-infected Akata cells, the objective recombinant virus vector can be produced in large quantities.

A non-virus vector for introducing the desired antisense nucleotide into target cells without using any recombinant viral vector can be produced by the gene transfer method using membrane fusion liposomes, for instance. This is a method for introducing the liposome contents directly into cells through the fusion activity to the cell membrane as given to membrane liposomes (small organelles having a lipid bilayer).

Antisense nucleotide introduction using the above-described membrane fusion liposomes can be carried out, for example, by the method of Nakanishi et al. [Nakanishi, M. et al., Exp. Cell. Res., 159, 399–499 (1985); Nakanishi, M. et al., Gene introduction into animal tissues. In Trends and Future Perspectives in Peptide and Protein Drug Delivery (ed. by Lee, V. H. et al.). Harwood Academic Publishers GmbH, Amsterdam, 1995, pp. 337–349].

In the following, the method of antisense nucleotide introduction by utilizing the above membrane fusion liposomes is described briefly.

Sendai virus, after gene inactivation with ultraviolet rays, and liposomes including the desired antisense nucleotide and high-molecular substances, such as expressed proteins, are fused together at 37° C. The membrane fusion liposomes have a structure, also called pseudovirus, with a liposome-derived cavity inside and the same spikes as the virus envelope outside. The membrane fusion liposomes are further purified by sucrose density gradient centrifugation and then allowed to be adsorbed on the target cultured cells or tissue cells at 4° C. Then, the temperature is raised to 37° C., when the liposome contents are introduced into the cells and the desired antisense nucleotide can be introduced into the target cells. The lipid component to be used here in preparing liposomes consists of 50% (mole ratio) cholesterol, lecithin and a negatively charged synthetic phospholipid, and unilamellar liposomes having a diameter of 300 nm are preferably prepared and used.

Another method of introducing the antisense nucleotide into target cells using liposomes is the antisense nucleotide introduction method using cationic liposomes. This method can be carried out according to the method of Yagi et al. [Yagi, K. et al., B.B.R.C., 196, 1042–1048 (1993)]. Paying attention to the fact that the plasmid as well as cells is negatively charged, this method comprises positively charging both the internal and external sides of the liposome membrane to thereby increase the uptake of the plasmid by means of static electricity and enhance the interaction thereof with the cells. Useful as the liposomes to be used here are positively charged multilamellar large vesicles (MLVs). It is also possible, however, to realize introduction of the object antisense nucleotide by using large unilamellar vesicles (LUVs) or small unilamellar vesicles (SUVs) and preparing composites thereof with the plasmid.

The method of preparing plasmid-including cationic MLVs is now described briefly. First, a chloroform solution containing lipid TMAG (N-(α-trimethylammonioacetyl)didodecyl D-glutamate chloride), DLPC (dilauroyl phosphatidylcholine) and DOPE (dioleoyl phosphatidylethanolamine) in a mole ratio of 1:2:2 (lipid concentration 1 mM) is prepared. Then, a total amount of 1 μmol of the lipid is placed in a Spitz test tube, and a thin lipid film is prepared by removing the chloroform in a rotary evaporator under reduced pressure. The film is dried by further thoroughly removing the chloroform under reduced pressure. Then, 0.5 ml of Dulbecco's phosphate-buffered saline containing Mg and Ca together with 20 μg of the plasmid for gene transfer is added and, after nitrogen gas substitution, the contents are stirred with a vortex mixer for 2 minutes, whereby a suspension of cationic MLVs can be obtained with the plasmid containing the object antisense nucleotide included therein.

In an example of the use, in gene therapy, of the plasmid-including cationic MLVs obtained in the above manner, 0.6 μg (as DNA) of the expression plasmid with the antisense nucleotide to be expressed inserted therein is embedded in the above cationic MLVs so that the liposome lipid amounts to 30 nmol. The resulting liposomes are suspended in 2 μl of phosphate-buffered saline, and the suspension is administered every other day to the target cells extracted from a patient or to a patient's tissue or tissues.

According to the definition in the relevant Japanese Ministry of Health and Welfare guideline, gene therapy is "to administer a gene or cells with a gene introduced therein intracorporeally to humans for the treatment of a disease". The term "gene therapy" as used herein includes, in addition to the above guideline definition, the treatment of various diseases, inclusive of cancer, by introducing the antisense nucleotide to the GASC1 gene into the above-mentioned target cells and, further, the treatment of various diseases by introducing the target gene or cells with the target gene introduced therein to the human body.

Method of Introducing the Gene of the Invention into Target Cells or a Target Tissue The method of introducing the object gene into the target cell or target tissue in the gene therapy of the invention includes the following representative two methods.

The first method comprises harvesting the target cells from a patient to be treated, growing the cells ex vivo, for example under addition of interleukin-2 (IL-2) or the like, to transfer the objective antisense nucleotide to the GASC1 gene as harbored in the retrovirus vector, and retransplanting the resulting cells (ex vivo method). This method is suitable for the therapy of ADA deficiency, genetic diseases caused by defective genes, cancer, and AIDS, for instance.

The second method is a method for direct gene transfer which comprises injecting the object antisense nucleotide (antisense nucleotide to the GASC1 gene) directly into the patient's body or the target site such as a tumor tissue (direct method).

More particularly, the first method can be carried out in the following manner, for instance. Thus, the mononuclear cells harvested from the patient are fractionally separated from monocytes using a blood sorter and the separated cells are cultured in the presence of IL-2 in a suitable medium such as AIM-V medium for about 72 hours, followed by addition of the vector harboring the antisense nucleotide (antisense nucleotide to the GASC1 gene) to be introduced. For enhancing the efficiency of transfer of the antisense nucleotide, the cells may be grown in the presence of protamine at 32° C. for 1 hour, centrifuged at 2500 ppm, and then cultured under 10% carbon dioxide gas at 37° C. for 24 hours. After this procedure is repeated a few times, the cells are further cultured in the presence of IL-2 in, for example, AIM-V medium for 48 hours and then washed with physiological saline. The viable cells are counted and the efficiency of introduction of the object antisense nucleotide is evaluated by the above-mentioned in situ PCR or, when the object is enzymatic activity, for instance, by assaying the degree of that activity.

The safety checks, such as culture of bacteria and fungi in cultured cells, check for the presence or absence of mycoplasma infection, search for endotoxin, etc. are carried out for safety confirmation. Thereafter, the cultured cells transformed with the predicted effective dose of the antisense nucleotide (antisense nucleotide to the GASC1 gene) are returned to the patient by intravenous drip injection. The above procedure is repeated at intervals of several weeks or a few months to consummate the gene therapy.

The dosage of the viral vector is judiciously selected according to the target cell. The usually preferred dose may for example be $1 \times 10^3$ cfu to $1 \times 10^8$ cfu in terms of virus titer per $1 \times 10^8$ target cells.

There can be adopted an alternative version of the above first method that comprises co-cultivating the virus-producer cells having the retrovirus vector harboring the object antisense nucleotide and the patient's cells to thereby introduce the antisense nucleotide (antisense nucleotide to the GASC1 gene) into the target cells.

In carrying out the second method (direct method) for gene therapy, it is particularly preferable to perform a preliminary experiment ex vivo to check whether the objective antisense nucleotide (antisense nucleotide to the GASC1 gene) can be actually introduced by the gene transfer method by carrying out PCR of the vector gene cDNA or in situ PCR or check whether the desired therapeutic effect, for example elevation of a specific activity or the growth or inhibition of growth of the target cell can be actually achieved by introduction of the objective antisense nucleotide (antisense nucleotide to the GASC1 gene). Moreover, when a viral vector is used, it is, of course, of great importance to confirm the safety of introduction of the antisense nucleotide in gene therapy by performing a PCR search for proliferative retrovirus and the like, determining the reverse transcriptase activity, or monitoring the coat protein (env) gene by the PCR technique.

An example of the gene therapy of the invention, especially when cancer or malignant tumor is the target, is a cancer therapy which comprises harvesting cancer cells from the patient, establishing a cultured cell line by enzymatic treatment or the like, introducing the object antisense nucleotide into the target cancer cells utilizing a retrovirus, for instance, carrying out a screening with G418 cells, then measuring the amount of expression of IL-12 or the like (in vivo), giving a radiation treatment, and inoculating the cells into the patient's tumor or paraneoplastic (tumor-associated) site(s).

Agent for Gene Therapy

The present invention further provides a pharmaceutical composition or preparation (a gene therapeutic agent) comprising an antisense nucleotide transfer vector of the invention or a cell line transformed/transfected with the antisense nucleotide (antisense nucleotide to the GASC1 gene) as an active ingredient in a pharmacologically effective amount in combination with a suitable pharmaceutical carrier or diluent.

The pharmaceutical carrier that can be utilized in the gene therapeutic agent of the invention includes those diluents or excipients, e.g. fillers, volume builders, binders, humectants, disintegrators, surfactants, lubricants, etc., which are usually employed depending on the mode of use of such a preparation, and these can be selectively used according to the contemplated unit dosage form of the preparation.

The unit dosage form of the gene therapeutic agent of the invention may be the same as mentioned for the pharmaceutical composition of the invention, and a suitable one can be selected according to the therapeutic objective.

The gene therapeutic agent of the invention, when it contains an antisense nucleotide transfer vector, for instance, is prepared in the form of liposomes with said vector embedded therein or in the form of cultured cells infected with a virus harboring a retrovirus vector containing the desired antisense nucleotide.

The agent for example be formulated in phosphate-buffered saline (pH 7.4), Ringer's solution or an intracellular composition injection or in such a dosage form as can be administered in combination with a substance conducive to an enhanced gene transfer efficiency, such as protamine.

The method of administering the above pharmaceutical preparation is not particularly restricted but a suitable regimen can be established according to the particular dosage form, the patient's age, sex and other factors, the severity of illness, and the like.

The amount of the active ingredient to be incorporated in the above pharmaceutical preparation and the dosage are not particularly restricted but each can be liberally selected from a broad range according to the expected therapeutic benefit, method of administration, duration of treatment, patient background inclusive of age and sex, and other variables.

Generally, the dosage of the retrovirus vector harboring the object antisense nucleotide as a pharmaceutical preparation may for example be about $1 \times 10^3$ pfu through about $1 \times 10^{15}$ pfu in terms of retrovirus titer per kilogram body weight per day.

In the case of cells carrying the antisense nucleotide for introduction, the dosage can be properly selected from the range of about $1 \times 10^4$ cells/body through $1 \times 10^{15}$ cells/body.

The above preparation can be administered once a day or in a few divided doses a day, or even intermittently at intervals of 1 or several weeks. Preferably, a substance conducive to an enhanced gene transfer efficiency, such as protamine, or a preparation containing the same can be administered in combination.

When the gene therapy according to the invention is applied to the therapy of cancer, it can be performed in a suitable combination with various gene therapies such as mentioned above (conjunctive gene therapy) and/or in combination with the conventional cancer chemotherapy, radiation treatment, immunotherapy, etc. The gene therapy of the invention can be performed with reference to the NIH guidelines, inclusive of its safety aspect [Recombinant DNA Advisory Committee, Human Gene Therapy, 4, 365–389 (1993)].

Detection of the Gene of the Invention and Cancer Diagnosis

In accordance with the invention, for the purpose of detecting the occurrence of the GASC1 gene which promotes tumorigenesis of cells, it is possible to prepare a biological sample such as blood or serum, optionally extract the nucleic acid, and analyze it for the occurrence or absence of a GASC1-sensitive gene. In accordance with the invention, it is also possible to prepare a biological sample having some or other disorder and analyze it for the occurrence or absence of a GASC1-associated neoplasm gene for detecting a neoplasm in cells or a tissue, the advance to a malignant prodromic disorder and/or the occurrence thereof as a prognostic index. By using this method, it becomes possible to detect a neoplasm in cells or a tissue, the progress to a malignant prodromic disorder or the occurrence thereof as a prognostic index and, thus, the diagnosis of such, for example cancer diagnosis and judgment of the effect of cancer therapy, and prognosis thereof become possible.

For example, the above detection method may comprise preparing a DNA fragment of the GASC1 gene based on the information concerning the GASC1 gene obtained from a sample from a patient with a tumor and designing it so that it may be used in the screening for the GASC1 gene and/or its amplification. More specifically, it is possible to construct a DNA fragment having the properties of a probe for use in plaque hybridization, colony hybridization, Southern blotting, Northern blotting, etc. or of a probe for the preparation of a full-length or partial DNA of the GASC1 gene as amplified by the polymerase chain reaction (PCR) which amplifies a nucleotide sequence with a polymerase. For this purpose, a primer having the same sequence as at least a part of the GASC1 gene is first prepared. The primer is then reacted, as a probe for screening, with a biological sample (nucleic acid sample), whereby the sample can be checked for the presence of the GASC1 gene sequence in the sample. The nucleic acid sample may be prepared by any of various techniques facilitating detection of the target sequence, such as denaturation, restriction digestion, electrophoresis, or dot blotting.

As the above screening method, the use of a PCR technique is particularly preferred from sensitivity points of view, and this technique is not particularly restricted inasmuch as a fragment of the GASC1 gene is used as a primer. Thus, any of the hitherto-known techniques (Science, 230, 1350–1354 (1985)) and the modified versions of PCR which have been developed of late or will be developed in the future (Sakaki, Yoshiyuki et al. (ed.), Jikken Igaku (Experimental Medicine), Supplement 8(9) (1990), Yōdosha; Protein, Nucleic Acid, Enzyme: Special Supplement, Kyoritsu Shuppan, 35(17) (1990)) may be used.

The DNA fragment for use as the primer is a chemically synthesized oligo-DNA, and such oligo-DNA can be synthesized using an automated DNA synthesizer or the like, for example Pharmacia LKB Gene Assembler Plus (Pharmacia). The preferred length of the primer (sense primer or antisense primer) to be synthesized may for example be about 10–30 nucleotides. The probe for us in the above-mentioned screening is usually a labeled probe but may be an unlabeled one, or the detection may be made according to specific binding to a directly or indirectly labeled ligand. The suitable label and the method of labeling the probe or ligand are known in the field of art to which the present invention belongs. Thus, the prior art label includes radioisotopes, biotin, fluorescent groups, chemiluminescent groups, enzymes, antibodies, etc., which can be taken up through known procedures such as nick translation, random priming and kinase treatment.

The PCR technique to be used for detection may for example be RT-PCR but various modifications of the technique which are in routine use in the art can be utilized.

Furthermore, the assay method of the invention can be expediently carried out by utilizing a reagent kit for detecting the GASC1 gene in samples.

The present invention thus provides a GASC1 gene detection reagent kit comprising a DNA fragment of the GASC1 gene.

The reagent kit comprises, as an essential component, at least a DNA fragment which hybridizes with a part or the whole of the nucleotide sequence shown in SEQ ID NO:1 or its complementary nucleotide sequence. It may optionally contain other components such as a labeling agent and PCR reagents (for example, Taq DNA polymerase, deoxynucleotide triphosphates, primers, etc.)

The labeling agent may be a radioisotope or a chemical modifier such as a fluorescent substance. In cases where the DNA fragment as such has been conjugated with such a labeling agent in advance, the kit need not contain such a labeling agent separately.

The reagent kit may further contain a suitable reaction diluent, standard antibody, buffer, wash solution, reaction stopper solution, etc. which make an assay easier to perform.

The present invention also provides a method for cancer diagnosis which comprises using the above assay method and a diagnostic agent or diagnostic reagent kit for use in practicing said method.

By directly or indirectly sequencing the GASC1 gene obtained from test samples by utilizing the assay method of the invention, it may become possible to find out new GASC1 gene-related genes having high homology to the wild-type GASC1 gene. Therefore, the present invention further provides a method of screening for human GASC1 gene-related genes in test samples which comprises performing such assay and sequencing the GASC1 DNA contained in the test samples.

The wild-type GASC1 and/or mutant GASC1 can be determined by utilizing the protein having the amino acid sequence shown in SEQ ID NO:3, namely the protein encoded by the human GASC1 gene, a protein having an amino acid sequence derived from the sequence shown in SEQ ID NO:3 by deletion, substitution or addition of one to several or a plurality of amino acids, a fragment of either of them, or an antibody to any of such proteins. Thus, the invention provides an antibody method and an antigen method for determining an anti-wild-type GASC1 and/or mutant GASC1.

By these methods, the degree of neoplastic state disorder or the malignancy of malignant tumor can be detected based on a change in the wild-type GASC1 polypeptide. Such change can be detected by GASC1 sequence analysis by the well-established technology described hereinabove, more preferably using an antibody (polyclonal or monoclonal antibody). Thereby, the difference(s) in the GASC1 protein or the presence or absence of the GASC1 protein can be detected.

More specifically, in carrying out the wild-type GASC1 and/or mutant GASC1 assaying method of the invention, the GASC1 protein is immunoprecipitated from a solution containing a biological sample obtained from a human body, such as blood or serum, using an anti-GASC1 antibody. Then, Western blot or immunoblot is carried out for the reaction with the GASC1 protein on a polyacrylamide gel.

When an anti-GASC1 antibody is utilized, the GASC1 protein in a paraffin-embedded or frozen tissue section can be detected by an immunohistochemical technique. The technologies to be used in the above assay and detection can appropriately be selected from among the antibody production and purification technologies well known in the art.

In preferred examples, the method for detecting the wild-type and/or mutant GASC1 includes enzyme-linked immunosorbent assay (ELISA), radioimmunoassay (RIA), immunoradiometric assay (IRMA), and immunoenzymometric assay (IEMA), inclusive of the sandwich technique, using a monoclonal antibody(ies) and/or a polyclonal antibody(ies).

Protein Receptor of the Invention and Pharmacoscreening

The invention can further provide a GASC1 receptor existing in a cell membrane fraction or on the cell surface and having binding affinity for the GASC1 protein.

The GASC1 receptor can be obtained by conjugating a labeled GASC1 protein in a biological sample containing a cell membrane fraction, extracting and isolating the GASC1 conjugation product, and identifying the amino acid sequence of the isolated product. The procedures for obtaining and sequencing the GASC1 receptor can be carried out in the manner conventional in this field of art.

The GASC1 receptor or a fragment thereof, preferably the GASC1 receptor, can be utilized in the technology of screening for any of various drugs. Thereby it is possible to screen for compounds (compounds which react with the GASC1 receptor, inclusive of low molecular compounds, high molecular compounds, proteins, partial protein fragments, antigens, antibodies, etc.). The GASC1 receptor (polypeptide or a fragment thereof; hereinafter the same shall apply) to be used in such screening tests may have been immobilized on a solid matrix.

An example of the above pharmacoscreening is a screening method which comprises reacting the test substance and the GASC1 protein, or a fragment thereof, competitively with the GASC1 receptor in a competitive binding assay and detecting the extent of inhibition of the complex formation between the GASC1 receptor and the GASC1 protein or its fragment by the substance under testing. Thus, the present invention provides a method for pharmacoscreening which comprises contacting a test substance with the GASC1 receptor for complex formation therebetween and determining the extent of inhibition, by the resulting complex, of the complex formation between the GASC1 receptor and the GASC1 protein, or a fragment thereof. A substance having inhibitory activity as obtained by this screening method can regulate the GASC1 activity itself through inhibition of the activity of the GASC1 receptor.

By labeling the GASC1 receptor and measuring amount of the label on the free (non-complex-forming) GASC1 receptor in the above competitive binding assay, it becomes possible for the measured value to serve as a yardstick of the binding of the test substance to the GASC1 receptor or as a measure of inhibition of the complex formation between the GASC1 receptor and the GASC1 protein.

The pharmacoscreening can be utilized also in screening for not only substances capable of inhibiting the activity of the GASC1 receptor but also compounds (peptides) having an adequate level of binding affinity for said receptor.

This procedure comprises synthesizing a large number of different test compounds on a solid support such as the surface of a plastic pin, then reacting the compounds with the GASC1 receptor and, after washing, detecting the binding reaction products by a known method [cf. e.g. PCT patent publication No. WO 84-03564]. In this procedure, the purified GASC1 receptor can be used by directly coating the same on an appropriate plate, or can also be used in a form captured by a non-neutralizing antibody against the polypeptide and thus immobilized on a solid phase.

Furthermore, the above screening method can also be utilized in a competitive pharmacoscreening assay. In this case, a neutralizing antibody capable of specifically binding to the GASC1 receptor is caused to competitive reaction with the test compound. Such a competitive reaction can detect the presence of any peptide having one or more antigenic determinants of the GASC1 receptor.

As a further method for drug screening, the method which uses a nonfunctional GASC1 gene-harboring eukaryotic host cell line may be mentioned. This method comprises growing the eukaryotic host cell line in the presence of a test compound for a certain period of time and then measuring the rate of growth of the host cells, whereby it is possible to confirm whether the test compound can bind to a protein regulating the growth and differentiation of the host cells to thereby control the concentration in blood and in tissues of the bound protein and the degree of migration thereof, for instance, or control the activity of that protein itself. One means for measuring the rate of growth of the host cells is to measure the biological activity of the GASC1 receptor.

In accordance with the present invention, it is also possible to design and produce another biologically active protein or a structural analogue, which interacts with the GASC1 protein, for example a GASC1 agonist, GASC1 antagonist, or GASC1 inhibitor. These are useful in developing a more active or stabilized derivative of the GASC1 protein or, for example, a drug capable of enhancing or suppressing the function of the GASC1 protein in vivo.

The sequence of such a structural analogue can be designed, for example, by identifying and analyzing the three-dimensional structure of the complex of the GASC1 protein and another protein by means of X ray crystallography, computer modeling or a combination of these. The information on the structure of the structural analogue can also be obtained by protein modeling based on the structures of homologous proteins.

As for the more active or stabilized derivative of the GASC1 protein, the region exerting an important influence on the activity or stability of the GASC1 protein can be realized, for example, by alanine scanning (alanine substitution) at least one of the amino acid residues constituting the GASC1 protein and determining the GASC1 activity of the peptide after alanine substitution. Further, a more active or stabilized derivative of the GASC1 protein can be obtained by substituting alanine for at least one amino acid residue in that region.

For obtaining a biologically active other protein or a structural analogue thereof capable of interacting with the GASC1 protein, it is also of use to isolate a target-specific antibody in advance by functional assaying and analyze the crystal structure thereof. This approach makes it possible to obtain a pharmacore which serves as a basis for designing a desired drug. By utilizing a functional anti-idiotype antibody to a pharmacologically active antibody, it becomes possible to select a desired peptide from among a peptide bank constructed by chemical or biological synthesis and accumulation. A peptide selected in this manner can be expected to serve as a pharmacore as well.

If the GASC1 protein can be obtained in large amounts in accordance with the present invention, it will be possible to utilize the protein in analytical studies such as X ray crystallography. Further, the GASC1 protein provided by the invention can be applied to the computer modeling technology in lieu of or in addition to X ray crystallography.

Furthermore, in accordance with the invention, it is possible, by constructing GASC1 gene-bearing knockout mice (transgenic mice), to ascertain which site or sites of the GASC1 gene sequence have influences on said multiple GASC1 activities in vivo, that is to say what functions the GASC1 gene expression product and of a modified GASC1 gene product have in vivo.

This method is a technique to intentionally modify the genetic information of a living body by utilizing homologous recombinant genes, and includes a method using mouse embryonic stem cells (ES cells) as an example [Capecchi, M. R., Science, 244, 1288–1292 (1989)].

The method of constructing such mutant mice is by now a routine technology in the relevant field of art [cf. e.g. Noda, Testuo (ed.): Jikken Igaku (Experimental Medicine), Supplement, 14(20) (1996), Yodosha]. By applying this technique to the wild-type GASC1 gene and mutant GASC1 gene, mutant mice can be produced with ease.

Establishment of an association between the mutant GASC1 gene sequence in the mutant mice obtained and the function thereof gives useful information in designing and developing GASC1 protein derivatives in a more active or stabilized form, such as mentioned above, in particular drugs functioning as GASC1 agonists, GASC1 antagonists or GASC1 inhibitors.

EFFECTS OF THE INVENTION

The invention provides a novel gene capable of regulating the growth and differentiation of various cells, tumorigenesis and transcriptional activation, among others. The gene is useful, for example, in elucidating the pathology of, diagnosing and/or treating diseases in which such activities are involved, for example malignant tumor, as mentioned below.

Like known oncogenes, the gene of the invention encodes two PHD finger motifs and one PX domain on the C terminal side of the relevant amino acid sequence. Further, amplification of the chromosome 9p23-24 region where the gene of the invention is located has been observed in a number of cancers. Analysis of the gene of the invention serves to elucidate the relation between the function of that gene and various diseases. Therefore, when this is utilized, the gene of the invention enables gene diagnosis of various diseases through examination of the state of expression of that gene in various tissues or analysis of the function thereof in vivo.

In accordance with the invention, it is possible to produce the protein encoded by the gene of the invention in large amounts in the manner of genetic engineering, and it is also possible to produce antibodies to that protein. The protein is useful in determining the GASC1 activity, the binding activity with the GASC1 receptor and other functions. The protein and antibodies thereto are useful in particular in pathology elucidation, diagnosis and treatment of diseases in which the GASC1 gene and the product thereof are involved, for example cancer.

Furthermore, the invention provides the antisense strand of the gene of the invention, a gene transfer vector useful in gene therapy which contains the same, cells harboring said vector, a gene therapeutic agent which comprises said vector or cells as an active ingredient, and a method for gene therapy which utilizes the same. In particular, the above gene therapy can be utilized in the treatment of various types of cancer through the growth inhibiting activity against various cancer cells.

BEST MODE FOR CARRYING OUT THE INVENTION

Figure 1:
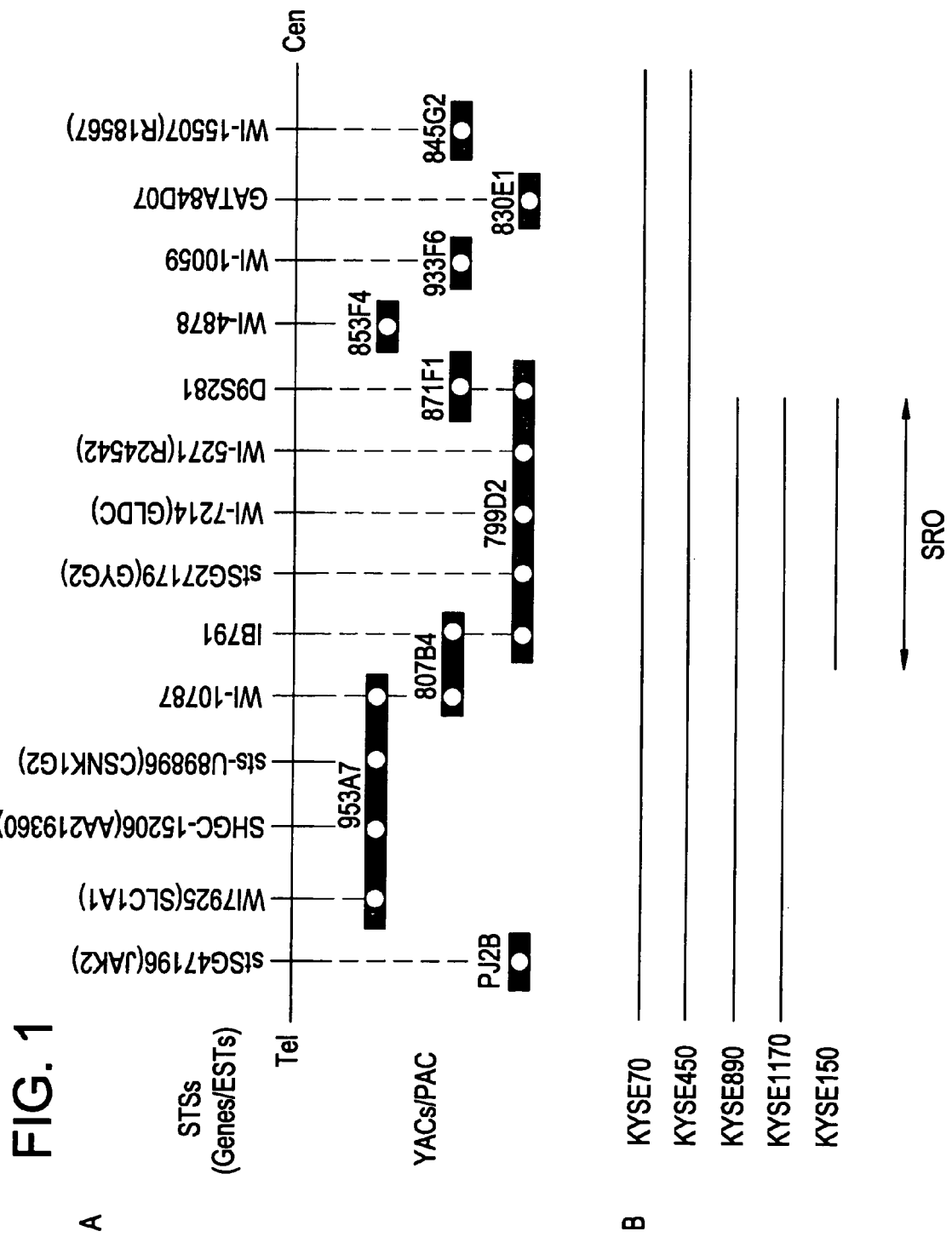
FIG. 1 is a schematic representation of the results of the FISH test described in Example 1-1. In the figure, A is a gene map of the 9p23-24 region surrounding the gene of the invention, and B schematically shows the sizes (lengths) of the 9p23 amplicons in five esophageal squamous cell carcinoma cell lines as identified by Southern blot analysis.

The following examples are given to illustrate the invention in further detail.

EXAMPLE 1

1. Materials and Methods

1) Esophageal Squamous Cell Carcinoma Cell Lines and Preparation of Metaphase Slides The 29 esophageal squamous cell carcinoma cell lines (KYSE series) used in the test are ones established from surgically excised tumors (Shimada, Y. et al., Cancer, 69, 277–284 (1992)). Copy number abnormalities in all of these cell lines have previously been confirmed by the present inventors. Metaphase chromosome slides were prepared according to the method of Shinomiya (Shinomiya, T. et al., Genes Chromosomes Cancer, 24, 337–344 (1999)) and used in a FISH test.

2) FISH Test Using YAC and PAC as Probes

The information on the location of the YAC in the specified region was collected from Whitehead Institute/MIT Genome Center, available via the internet through the world wide web (www) at "-genome.Wi.Mit.Edu/", and Resources for Human Molecular Cytogenetics, available via the internet through the world wide web (www) at "bioserver.uniba.it/FISH/rocchi/welcom.html".

A plurality of YAC clones covering the human 9p23-24 region were isolated from YAC library of the Centre d'Etude du Polymorphisme Humain (CEPH), and FISH probes were prepared therefrom by PCR using the Alu sequence in accordance with the above-mentioned method of Shinomiya et al.

This PCR was carried out in the following manner. Thus, the YAC DNA 1 μg (1 μl), the primer 2484 having the nucleotide sequence shown in SEQ ID NO:4 (30 μM) 1 μl, the primer PDJ34 having the nucleotide sequence shown in SEQ ID NO:5 (10 μM) 1 μl, 10×PCR buffer (ExTaq buffer, Takara Shuzo) 10 μl, 2.5 mM dNTPs (Takara Shuzo) 5 μl, ExTaq polymerase 0.5 μl and water 81.5 μl (total 100 μl) were mixed up and, following 4 minutes of treatment at 95° C. (first one denaturation treatment), the reaction was carried out in a total of 30 cycles (each cycle comprising 95° C.-4 minutes, 55° C.-1 minute, and 72° C.-4 minutes), followed by the final treatment (once) at 72° C. for 7 minutes. All the above reactions were carried out using Perkin-Elmer Gene-Amp PCR system 9700.

One PAC clone (gift from Dr. Peter Marynen) containing janua kinase 2 (JAK2, GenBank Accession No. NM-004972), a known gene mapped in 9p24, was used as a probe.

The above probe was labeled by nick translation using biotin 16-dUTP or digoxin 11-dUTP (Boehringer Mannheim). Fluorescence detection of chromosomal hybridization signals was carried out according to the above-mentioned method of Shinomiya et al.

After washing, the stained images and fluorescence signals on the slides were simultaneously imaged using CCD (cooled charge-coupled device) camera (KAF 1400; product of Photometrics).

Relative changes in DNA sequence copy number were analyzed using the IP Lab Spectrum software (product of Signal Analytics Corp.). The copy numbers of the necessary region were evaluated according to the hybridization patterns observed for the chromosomes both at the metaphase stage and at the resting stage. When the fluorescence intensity ratio exceeded 1.5, that chromosome region was judged to show a high level of amplification.

As a result, increases in copy number on 9p were detected in 5 (17.2%) out of the 29 esophageal squamous cell carcinoma cell lines investigated by the present inventors in a previous CGH analysis. A still higher level of amplification was found in one of them. Based on the results of this CGH, a FISH analysis was carried out in KYSE150 using 8 YACs and one PAC as probes.

3) Results

The results are shown in FIG. 1 (FIG. 1A and FIG. 1B).

In FIG. 1, A is a gene map of the 9p23-24 region including the gene of the invention and, in the figure, "STSs (Genes/ESTs)" stands for the sequence-tagged site (gene/expression sequence tag), "Tel" for the telomere side, "Cen" for the centromere side, and "YACs/PAC" for each probe used in FISH.

In FIG. 1A, known genes and transcripts identified by the respective expression sequence tags (EST) shown in the parentheses are shown on the line representing the chromosome. These were used as probes in Southern blotting.

The plurality of YACs (953A7, 807B4, 799D2, 871F1, 853F4, 933F6, 830E1 and 845G2) and one PAC (PJ2B) used in the FISH are indicated by horizontal black lines interrupted by one or more white small circles, respectively below the chromosome-indicating line. The small circles in these horizontal lines respectively indicate the points of fixation of the markers on the YACs or PAC. This figure is a schematic one, hence it does not reflect the actual sizes of the YACs and PAC or the actual marker-to-maker distances.

FIG. 1B is a schematic representation of the 9p23 amplicons in the five respective esophageal squamous cell carcinoma cell lines (in the figure, shown as KYSE70, KYSE450, KYSE890, KYSE1170 and KYSE150) specified in a Southern blot analysis (shown approximately corresponding to the chromosome-indicating line in FIG. 1A). In the figure, the region of smallest overlapping (SRO) was specified by FISH, together with the results of Southern blot analysis.

Figure 2:
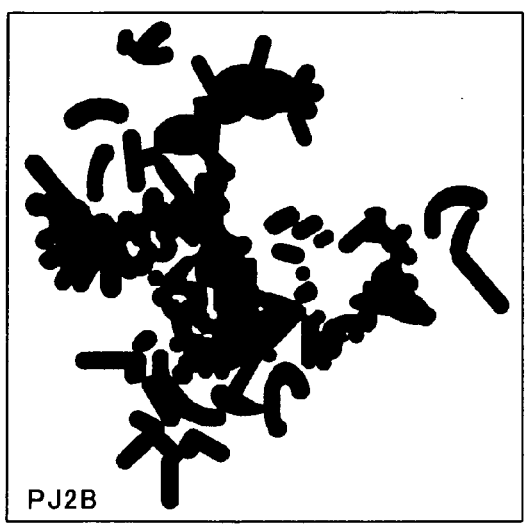
FIG. 2 is a representation of typical results of the FISH analysis as described in Example 1-1, in KYSE150, which is an esophageal squamous cell carcinoma cell line.
Figure 2:
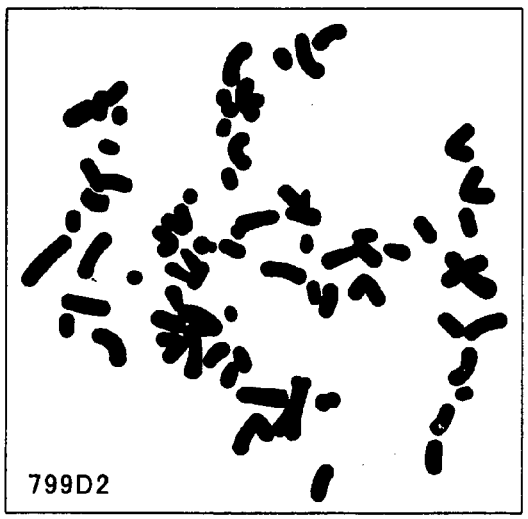
Figure 2:
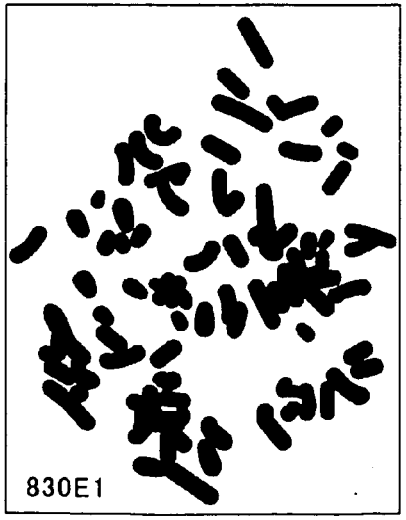

FIG. 2 is a representation of typical results of the FISH analysis in KYSE 150, one of the above-mentioned esophageal squamous cell carcinoma cell lines.

In that figure, the results of the FISH carried out using the PACPJ2B, YAC799D2 and YAC830E1 clones are respectively shown from top to bottom. In each representation, the number of fluorescent spots indicates the DNA copy number. In each representation, the abbreviations PJ2B, 799D2 and 830E1 are the same as those shown in FIG. 1A.

As shown in FIG. 2, YAC799D2 produced intense signals as homogeneously staining regions (HSRs) on two marker chromosomes. This indicates that a high level of amplification occurred in the region in which YAC799D2 is included. In the case of 807B4, the FISH carried out in the same manner gave the same results (not shown).

The numbers of FISH signals in YAC953A7, 871F1, 853F4 and 933F6 occurring on both sides of YAC799D2 (cf. FIG. 1A) ranged from 4 to 9. These are, however, by far smaller as compared with YAC799D2 and 807B4. With PACPJ2B and YAC830E1, the copy numbers were only 2 to 3.

For identifying the common region showing the lowest level of amplification within the 9p23-24 region, other 4 cell lines (KYSE70, 450, 890 and 1170), which showed increases in copy number on 9p in the previous CGH analysis, were also subjected to FISH analysis.

As a result, hybridization signals of YAC799D2 and 807B4 were detected as small HSR patterns in KYSE890 and 1170. On the other hand, the number of signals was about 6 to 9 in KYSE70 and 450. In these cell lines, however, broader regions were amplified than the amplification region detected in KYSE150, so that the amplicon size determined in KYSE150 could not be narrowed.

It was thus estimated that the desired gene in the 9p23-24 region amplicons should occur in a relatively narrow region covered by YAC799D2 and 807B4.

2. Southern Blot Analysis and Northern Blot Analysis

Eight EST clones ((1) GYG2, (2) GLDC, (3) IMAGE clone 131865 (GenBank Accession No. R24542), (4) SLC1A1, (5) CSNK1G2, (6) JAK2, (7) IMAGE clone 650495 (GenBank Accession No. AA219360) and (8) IMAGE clone 30354 (GenBank Accession No. R18567); the above clones (1), (2) and (4)-(6) each is a part of a known gene and (3), (7) and (8) each is a part of a transcript) in the 9p23-24 region as selected from Whitehead Institute for a genome research database were purchased from Research Genetics and used as probes for Southern blot and Northern blot analyses.

Tumor DNA was extracted from each esophageal squamous cell carcinoma cell line cultured by a standardized method (reference: Sambrook, J. et al., Molecular Cloning, A Laboratory Manual, 2nd Ed., Cold Spring Harbor Laboratory Press, 1989).

For the Southern blot analysis, 10 µg of DNA extracted from each cell line or normal lymphocytes and digested with EcoRI was subjected to electrophoresis on a 0.8% agarose gel, followed by transfer onto a polyamide membrane (BIO-DYNE B, product of Nihon Pall). For the Northern blot analysis, 20 µg of total RNA extracted from each cell line was subjected to electrophoresis on a 1.0% agarose/0.67 M formaldehyde gel, followed by transfer onto a polyamide membrane (Hybond-N+, product of Amersham Pharmacia Biotech).

After transfer, each membrane was hybridized with each EST probe labeled with $[\alpha^{32}P]dCTP$, under appropriate conditions and, after washing, used for exposure of a Kodak X-OMAT film according to the above-mentioned method of Shinomiya.

For comparing the expression patterns in different human normal tissues, Northern blots prepared by using RNAs extracted from 12 different tissues (MTN-human 12 lanes; product of Clontech) were hybridized with the IMAGE clone 131865 (GenBank accession number R24542) labeled with $[(\alpha^{32}P]dCTP$.

The Southern blot analysis was carried out under the following conditions:
1) Prehybridization and hybridization buffers: PEG/SDS solution (7% PEG 8000, 10% SDS) containing denatured salmon sperm DNA (200 mg/ml) and human placental DNA (200 mg/ml);
2) Prehybridization conditions: 12–16 hours at 65° C. with continuous stirring;
3) Hybridization conditions: 12–16 hours at 65° C. with continuous stirring;
4) Washing: with washing solution 1 (2×SSC, 0.1% SDS), 15 minutes at 55° C. with continuous stirring, and then with washing solution 2 (0.1×SSC, 0.1% SDS), 15 minutes at 55° C. with continuous stirring, followed by rinsing with 2×SSC.

The Northern blot analysis was carried out under the following conditions:
1) Prehybridization and hybridization buffers: ExpressHyb (Clontech) was used;
2) Prehybridization conditions: 30 minutes at 68° C. with continuous stirring;
3) Hybridization conditions: 1 hour at 68° C. with continuous stirring;
4) Washing: with washing solution 1 (2×SSC, 0.1% SDS), 30 minutes at 55° C. with continuous stirring, and then with washing solution 2 (0.1×SSC, 0.1% SDS), 15 minutes at 55° C., twice, with continuous stirring, followed by rinsing with 2×SSC.

As a result, the Southern blot analysis of the esophageal squamous cell carcinoma cell lines using three EST probes, namely glycogenin 2 (GYG2) and glycine dehydrogenase (GLDC) localized on YAC799D2, and IMAGE clone 131865 (GenBank Accession No. R24542), showed amplification patterns in the 5 cell lines which had showed an increase in copy number on 9p in the CGH and FISH tests.

On the contrary, it was revealed that the probes for out-of-region genes or unknown transcripts, namely SLC1A1, one of the solute-carrier family, JAK2, casein kinase 1γ2 (CSNK1G2), IMAGE clone 650495 (GenBank Accession No. AA219360) and IMAGE clone 350354 (GenBank Accession No. R18567), show no amplification in KYSE150 (for these probes, refer to FIG. 1B).

Figure 3:
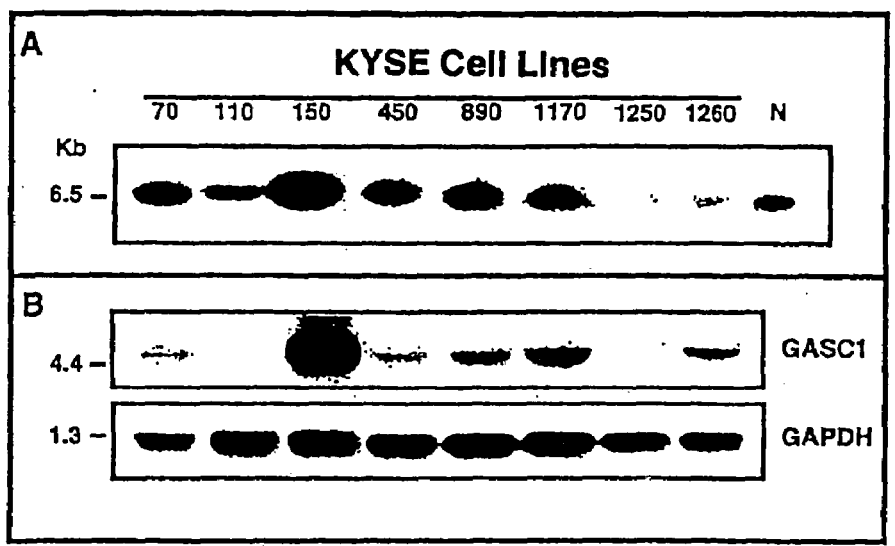
FIG. 3 is a representation of the results of the test described in Example 1-2. In the Figure, A shows the extents of amplification of GASC1 in various esophageal squamous cell carcinoma cell lines, and B shows the results of Northern blot analysis using RNAs from various esophageal squamous cell carcinoma cell lines, illustrating an excessive expression of GASC1.

Upon rough estimation of the degrees of amplification based on the comparison in hybridization signal between esophageal squamous cell carcinoma cell line DNA and normal DNA, it was revealed that the first three probes (GYG2, GLDC, IMAGE clone 131865) showed at least 12-fold amplification in KYSE150; and 3 to 6-fold amplification was confirmed in the other four cell lines (cf. FIG. 3A).

FIG. 3A shows the amplifications of GASC1 in the esophageal squamous cell carcinoma cell lines. This figure was obtained by Southern blotting using IMAGE clone 131865 as the probe in the manner described above.

From the figure, it is seen that the signal on the normal human peripheral blood lymphocyte-derived DNA (N) is weaker than KYSE70, 150, 450, 890 and 1170, among the 8 esophageal squamous cell carcinoma cell lines, stronger than 1250 and 1260, and comparable to 110. This indicates that IMAGE clone 131865 was amplified in KYSE70, 150, 450, 890 and 1170.

FIG. 3B shows the results of Northern blot analysis as obtained by subjecting total RNA of each of the same eight esophageal squamous cell carcinoma cell lines as used in FIG. 3A to hybridization using IMAGE clone 131865 (GASC1) or a control (GAPDH) as the probe.

From the figure, it is evident that the GASC1 gene was excessively expressed in the five esophageal squamous cell carcinoma cell lines showing amplification in FIG. 3A (KYSE70, KYSE150, KYSE450, KYSE890 and KYSE1170).

Figure 4:
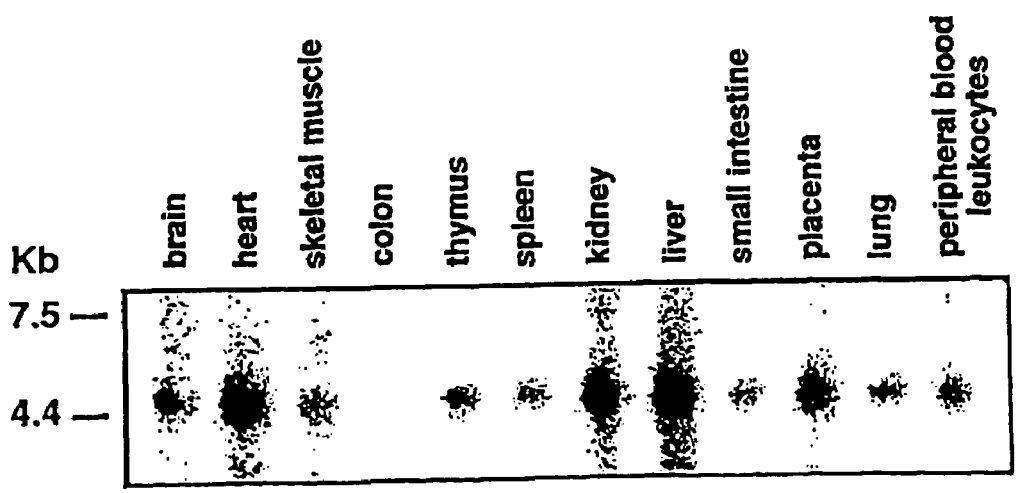
FIG. 4 is a representation of the results of the test described in Example 1-2, showing the results of examination of the expression patterns of the gene of the invention in various normal human tissues.

Further, FIG. 4 shows the results of an examination of the expression of the gene of the invention in normal human tissues.

This figure shows the results produced by hybridizing the Northern blots produced using RNA samples extracted from 12 different tissues with IMAGE clone 131865 labeled with [$\alpha^{32}$P]dCTP. The hybridization procedure used was the same as in the case of FIG. 3B.

From the above findings, discussion may be made as follows.

The results of the Northern blot carried out for analyzing the levels of expression of the three unknown transcripts (IMAGE clone 131865, 650495 and 30354) revealed that the IMAGE clone 131865 alone showed excessive expression in cell lines showing amplification on 9p23-24 (cf. FIG. 3B).

This result indicates that the IMAGE clone 131865 is a part of the candidate amplification target gene occurring within this amplicon. Therefore, the full-length gene was cloned using this clone and the sequence thereof was determined.

The Northern blots produced by using RNA from a plurality of human normal tissues that hybridized with the IMAGE clone 131865 revealed the expression of a 4.5 Kb one signal transcript in all the tissues (cf. FIG. 4).

3. cDNA Library Screening and DNA Sequence Determination

Two cDNA libraries were constructed from RNA of a stomach carcinoma cell line (HSC39) using the oligo cap method (Maruyama, K. et al., Gene, 138, 171–174 (1994)) and the ZAP-cDNA GigaPACK III Gold cloning kit (Stratagene).

Each library was subjected to screening using, as the probe, the IMAGE clone 131865 (a partial sequence of which is known, that sequence having GenBank Accession No. R24542)

As a result of such screening, six overlapping cDNA clones were isolated, and their DNA sequences were determined using a model 377 ABI automated sequencer (PE Biosystems). In this way, a transcript consisting of 4253 nucleotides was found.

The transcript agreed well in size to the one indicated by the Northern blot analysis, hence this cDNA was estimated to be the full-length cDNA.

Upon nucleic acid sequence analysis, the consensus sequence for transcription initiation (Kozak's rule) was found well conserved, hence it was supposed that the transcription should start at the 147th nucleotide. Two AATAA (SEQ ID NO:10) polyadenylation signals were found at the 3' end continued by poly(A) extension. Thus, the amino acid sequence of the deduced protein was identified as comprising the 1056 amino acid residue sequence as shown in SEQ ID NO:3.

The region from the 10th to the 3140th nucleotide out of the DNA sequence of GASC1 (shown in SEQ ID NO:1) showed marked homology to the cDNA portion of KIAA0780 (GenBank Accession No. AB018323).

Furthermore, for confirming the sequence of the isolated clone, a reverse transcription PCR (RT-PCR) analysis was carried out using, as the template, RNA from each of the five esophageal squamous cell carcinoma cell lines (KYSE-70, KYSE-150, KYSE-450, KYSE-890 and KYSE-1170) that had showed excessive expression, together with two pairs of primers shown below as prepared based on the sequence determined from a clone isolated by screening the clone 131865.

The sequences of the primers used in such RT-PCR are shown in SEQ ID NO:6 to SEQ ID NO:9.

Primer W1f: SEQ ID NO:6
Primer W1r: SEQ ID NO:7
Primer W2f: SEQ ID NO:8
Primer W2r: SEQ ID NO:9

The RT (reverse transcription) reaction was carried out by mixing 1 μg of RNA with 0.5 μg of oligo(dT) primer (total amount 10 μl) and, after 10 minutes of denaturation treatment at 70° C., adding 4 μl of 5× reverse transcription buffer (GIBCO), 1 μl of RNase inhibitor (TOYOBO) and 4 μl of 2.5 mM dNTPs (TAKARA) (total amount 19 μl), further adding 1 μl of Superscript II (GIBCO), and incubating the mixture at 42° C. for 45 minutes.

The PCR was carried out utilizing GeneAmp PCR system 9700 (Perkin-Elmer). The reaction was carried out by adding 2 μl of 10×ExTaq buffer (TAKARA), 1.0 μl of 2.5 mM dNTPs (TAKARA), 0.5 μl of 10 μM each primer and 0.5 U of ExTaq (TAKARA) to 1 μl of the RT product and making the total amount 20 μl. As for the conditions, the initial denaturation was carried out at 94° C. for 2 minutes, followed by 25 cycles each comprising 30 seconds at 94° C., 30 seconds at 58° C. and 30 seconds at 72° C. and further followed by additional 7 minutes for the extension reaction at 72° C.

As a result, it was found that a single band product had been produced that had a predicted size by which the sequence determined can be confirmed to be correct. In addition, a DNA fragment comprising from the 238th to the 638th nucleotide out of the DNA sequence as produced by RT-PCR using W2f and W2r as probes was labeled with [$\alpha^{32}$P]dCTP and hybridized with a polyamide membrane (BIODYNE B, product of Nihon Pall) spotted with YAC799D2 containing the IMAGE clone (R24542), whereupon a signal was detected and, furthermore, amplified signals were shown on all the Southern blots of the five tumor cell lines (KYSE70, KYSE150, KYSE450, KYSE890 and LYSE1170) showing amplification in the 9P23-24 region.

Analysis of the estimated amino acid sequence suggested that the gene product contains two PHD fingers and one PX domain (the sequences from the 687th to the 749th and from the 806th to the 867th out of the amino acid sequence shown in SEQ ID NO:3 being the finger sequences, and the amino acid sequence from the 980th to the 1047th being the PX domain sequence).

In a computer prediction about the intracellular localization thereof using the PSORT II program (reference: http://psort.nibb.ac.jp/form2.html), one typical doublet nuclear localization signal was detected on the 979th to 996th amino acids in the GASC1 protein, suggesting the localization in the nucleus.

In view of the results mentioned above, the GASC1 gene containing the PHD finger motifs, which are motifs suggesting its being a candidate "oncogene", and the PX domain is supposed to play an important role in the genesis and advancement, among others, of various tumors, and it is strongly suggested that said gene should be a tumor-associated gene (inclusive of a candidate oncogene) associated with the genesis and/or progress of various types of tumor, inclusive of esophageal squamous cell carcinoma as well, upon increased expression of the GASC1 transcript in the chromosome 9p23-24 region.

INDUSTRIAL APPLICABILITY

The invention provides a novel gene, namely GASC1 gene, having activity in regulating the growth and differentiation of various cells, tumorigenesis and transcriptional activation, among others. By utilizing this gene, it becomes possible to elucidate the pathology of diseases associated with said activity, for example malignant tumors, and/or carry out diagnosis and treatment thereof, among others.

The invention claimed is:

1. An isolated polynucleotide comprising a nucleotide sequence encoding the amino acid sequence shown in SEQ ID NO:3, or a complement of said nucleotide sequence.

2. The isolated polynucleotide according to claim 1, wherein said polynucleotide comprises the nucleotide sequence shown in SEQ ID NO:1 or a complement of said nucleotide sequence shown in SEQ ID NO:1.

3. A recombinant expression vector comprising the isolated polynucleotide of claim 1 or 2.

4. An isolated host cell harboring the recombinant expression vector of claim 3.

5. A primer set consisting of (a) an oligonucleotide of either SEQ ID NO:6 or SEQ ID NO:8, and (b) an oligonucleotide of either SEQ ID NO:7 or SEQ ID NO:9.

6. A composition comprising the primer set of claim 5 and a diluent.

* * * * *

SEQUENCE LISTING

<160> NUMBER OF SEQ ID NOS: 10

<210> SEQ ID NO 1
<211> LENGTH: 3168
<212> TYPE: DNA
<213> ORGANISM: Homo sapiens

<400> SEQUENCE: 1

```
atggaggtgg ccgaggtgga aagtcctctg aaccccagct gtaagataat gaccttcaga      60
ccctccatgg aggagttccg ggagttcaac aaataccttg catacatgga gtctaaagga     120
gcccatcgtg cgggtcttgc aaaggtgatt cctcctaagg agtggaagcc aagacagtgc     180
tatgatgaca ttgataattt gctcattcca gcaccaattc agcagatggt cacagggcag     240
tcaggactgt tcactcagta caacatccag aaaaaagcga tgactgtgaa ggagttcagg     300
cagctggcca acagtggcaa atattgtact ccaagatact tggattacga agatttggag     360
cgcaagtact ggaagaactt aacttttgtg gcacctatct atggtgcaga tattaatggg     420
agcatatatg atgagggtgt ggatgaatgg aacatagctc gcatcaatac agtcttggat     480
gtggttgaag aagagtgtgg catttctatt gagggtgtaa ataccccata tctctatttt     540
ggcatgtgga agaccacgtt tgcatggcac accgaagaca tggacctcta tagcattaat     600
tatctccact ttggagagcc caagtcttgg tatgctatac ctccggagca tggaaaacga     660
cttgaaagac tagctcaagg ttttttccca agcagctccc aagggtgtga tgcatttctt     720
cgccacaaga tgacattgat ttctccatca gtattgaaga aatatggtat tcccttttgac     780 aagataaccc aggaggctgg agaattcatg atcactttcc catatggcta ccatgctggt     840
tttaatcatg gtttcaactg tgcagaatct acaaattttg ctactgtcag atggattgac     900
tatggaaaag ttgccaaatt gtgcacttgc aggaaagaca tggtgaagat ttcaatggat     960
atctttgtga ggaaatttca gccagacaga tatcagcttt ggaaacaagg aaaggatata    1020
tacaccattg atcacacgaa gcctactcca gcatccaccc ctgaagtaaa agcatggctg    1080
cagaggagga ggaaagtaag aaaagcatcc cgaagcttcc agtgtgctag gtctacctct    1140
aaaaggccta aggctgatga ggaagaggaa gtgtcagatg aagtcgatgg ggcagaggtc    1200
cctaaccccg actcagtcac agatgacctc aaggtcagtg aaaagtcaga agcagcagtg    1260
aagctgagga acacagaagc atcttcagaa gaagagtcat ctgctagcag gatgcaggtg    1320
gagcagaatt tatcagatca tatcaaactc tcaggaaaca gctgcttaag tacatctgta    1380
acagaagaca taaaaactga ggatgacaaa gcttatgcat atagaagtgt accttctata    1440
tccagtgagg ctgatgattc cattccattg tctactggct atgagaagcc cgagaaatca    1500
gacccatccg agctttcatg gccaaagtca cctgagtcat gctcatcagt ggcagagagt    1560
aatggtgtgt taacagaggg agaagagagt gatgtggaga gccatgggaa tggccttgaa    1620
```

-continued

```
cctgggaaa tcccagcggt ccccagtgga gagagaaata gcttcaaagt ccccagtata    1680
gcagagggag agaacaaaac ctctaagagt tggcgccatc cacttagcag gcctccagca    1740
agatctccga tgactcttgt gaagcagcag gcgccaagtg atgaagaatt gcctgaggtt    1800
ctgtccattg aggaggaagt ggaagaaaca gagtcttggg cgaaacctct catccaccttt   1860 tggcagacga agtcccctaa cttcgcagct gagcaagagt ataatgcaac agtggccagg    1920
atgaagccac actgtgccat ctgcactctg ctcatgccgt accacaagcc agatagcagc    1980
aatgaagaaa atgatgctag atgggagaca aaattagatg aagtcgttac atcggaggga    2040
aagactaagc ccctcatacc agagatgtgt tttatttata gtgaagaaaa tatagaatat    2100
tctccaccca atgccttcct tgaagaggat ggaacaagtc tccttatttc ctgtgcaaag    2160
tgctgcgtac gggttcatgc aagttgttat ggtattcctt ctcatgagat ctgtgatgga    2220
tggctgtgtg cccggtgcaa agaaatgcg tggacagcag aatgctgtct ctgcaatttg      2280
agaggaggtg ctcttaagca acgaagaac aataggtggg cccatgtcat gtgcgccgtt      2340
gcggtcccag aagttcgatt cactaatgtc ccagaaagga cacaaataga tgtaggcaga    2400 ataccttta agaggttaaa attgaaatgc atcttctgca gacaccgggt taagagggtc      2460
tctggagcct gcatccagtg ttcctacggt cgctgcccgg cctccttcca tgtcacttgt    2520
gcccatgctg ctggggtact gatggagcct gatgattggc cttatgtggt gaacattaca    2580
tgctttcgac ataaggtcaa ccccaacgtg aagtccaagg cttgcgagaa ggtcatttcc    2640
gtgggtcaaa cggtcatcac gaagcatcgg aacacccggt attacagttg cagagtgatg    2700
gctgtgacat cgcagacctt ctatgaggtc atgtttgatg atggctcctt tagcagagac    2760
acatttcctg aggatatcgt gagccgagac tgtctgaagc tgggcccacc tgctgaggga    2820
gaagtcgtcc aagtcaagtg gcccgatggc aaactctatg gagcaaaata ttttggatca    2880
aatattgccc acatgtacca ggttgagttt gaagatggat cccagatagc aatgaagaga    2940
gaggacatct acactttaga tgaagagtta cccaagagag tgaaagctcg attttccaca    3000
gcctctgaca tgcgatttga agacacgttt tatggagcag acattatcca aggggagaga    3060
aagagacaaa gagtgctgag ctccaggttt aagaatgaat atgtggccga ccctgtatac    3120 cgcactttt tgaagagctc tttccagaag aagtgccaga agagacag                  3168
```

<210> SEQ ID NO 2
<211> LENGTH: 4253
<212> TYPE: DNA
<213> ORGANISM: Homo sapiens
<220> FEATURE:
<221> NAME/KEY: CDS
<222> LOCATION: (147)..(3314)

<400> SEQUENCE: 2

```
cggcacgaga acagctgtca cctagtgcgg aacaagtctc ccaaatttcc caaatctccc     60
tgggccggag gccactgtct tctcttcctc ctccaccgag tcgtgctctc gccccaaccc    120
gcgcgccaga cactgcccta accatc atg gag gtg gcc gag gtg gaa agt cct    173
                            Met Glu Val Ala Glu Val Glu Ser Pro
                              1               5 ctg aac ccc agc tgt aag ata atg acc ttc aga ccc tcc atg gag gag    221
Leu Asn Pro Ser Cys Lys Ile Met Thr Phe Arg Pro Ser Met Glu Glu
 10              15                  20                  25 ttc cgg gag ttc aac aaa tac ctt gca tac atg gag tct aaa gga gcc    269
Phe Arg Glu Phe Asn Lys Tyr Leu Ala Tyr Met Glu Ser Lys Gly Ala
             30                  35                  40
```

-continued

| | | |
|---|---|---|
| cat cgt gcg ggt ctt gca aag gtg att cct cct aag gag tgg aag cca<br>His Arg Ala Gly Leu Ala Lys Val Ile Pro Pro Lys Glu Trp Lys Pro<br>              45                    50                  55 | 317 |
| aga cag tgc tat gat gac att gat aat ttg ctc att cca gca cca att<br>Arg Gln Cys Tyr Asp Asp Ile Asp Asn Leu Leu Ile Pro Ala Pro Ile<br>      60                   65                70 | 365 |
| cag cag atg gtc aca ggg cag tca gga ctg ttc act cag tac aac atc<br>Gln Gln Met Val Thr Gly Gln Ser Gly Leu Phe Thr Gln Tyr Asn Ile<br>75                    80                85 | 413 |
| cag aaa aaa gcg atg act gtg aag gag ttc agg cag ctg gcc aac agt<br>Gln Lys Lys Ala Met Thr Val Lys Glu Phe Arg Gln Leu Ala Asn Ser<br>90                95               100          105 | 461 |
| ggc aaa tat tgt act cca aga tac ttg gat tac gaa gat ttg gag cgc<br>Gly Lys Tyr Cys Thr Pro Arg Tyr Leu Asp Tyr Glu Asp Leu Glu Arg<br>              110               115             120 | 509 |
| aag tac tgg aag aac tta act ttt gtg gca cct atc tat ggt gca gat<br>Lys Tyr Trp Lys Asn Leu Thr Phe Val Ala Pro Ile Tyr Gly Ala Asp<br>             125               130             135 | 557 |
| att aat ggg agc ata tat gat gag ggt gtg gat gaa tgg aac ata gct<br>Ile Asn Gly Ser Ile Tyr Asp Glu Gly Val Asp Glu Trp Asn Ile Ala<br>         140              145             150 | 605 |
| cgc atc aat aca gtc ttg gat gtg gtt gaa gaa gag tgt ggc att tct<br>Arg Ile Asn Thr Val Leu Asp Val Val Glu Glu Glu Cys Gly Ile Ser<br>155                   160              165 | 653 |
| att gag ggt gta aat acc cca tat ctc tat ttt ggc atg tgg aag acc<br>Ile Glu Gly Val Asn Thr Pro Tyr Leu Tyr Phe Gly Met Trp Lys Thr<br>170                 175              180             185 | 701 |
| acg ttt gca tgg cac acc gaa gac atg gac ctc tat agc att aat tat<br>Thr Phe Ala Trp His Thr Glu Asp Met Asp Leu Tyr Ser Ile Asn Tyr<br>             190               195             200 | 749 |
| ctc cac ttt gga gag ccc aag tct tgg tat gct ata cct ccg gag cat<br>Leu His Phe Gly Glu Pro Lys Ser Trp Tyr Ala Ile Pro Pro Glu His<br>         205              210             215 | 797 |
| gga aaa cga ctt gaa aga cta gct caa ggt ttt ttc cca agc agc tcc<br>Gly Lys Arg Leu Glu Arg Leu Ala Gln Gly Phe Phe Pro Ser Ser Ser<br>220                   225              230 | 845 |
| caa ggg tgt gat gca ttt ctt cgc cac aag atg aca ttg att tct cca<br>Gln Gly Cys Asp Ala Phe Leu Arg His Lys Met Thr Leu Ile Ser Pro<br>235                   240              245 | 893 |
| tca gta ttg aag aaa tat ggt att ccc ttt gac aag ata acc cag gag<br>Ser Val Leu Lys Lys Tyr Gly Ile Pro Phe Asp Lys Ile Thr Gln Glu<br>250                   255              260             265 | 941 |
| gct gga gaa ttc atg atc act ttc cca tat ggc tac cat gct ggt ttt<br>Ala Gly Glu Phe Met Ile Thr Phe Pro Tyr Gly Tyr His Ala Gly Phe<br>             270               275             280 | 989 |
| aat cat ggt ttc aac tgt gca gaa tct aca aat ttt gct act gtc aga<br>Asn His Gly Phe Asn Cys Ala Glu Ser Thr Asn Phe Ala Thr Val Arg<br>         285              290             295 | 1037 |
| tgg att gac tat gga aaa gtt gcc aaa ttg tgc act tgc agg aaa gac<br>Trp Ile Asp Tyr Gly Lys Val Ala Lys Leu Cys Thr Cys Arg Lys Asp<br>         300              305             310 | 1085 |
| atg gtg aag att tca atg gat atc ttt gtg agg aaa ttt cag cca gac<br>Met Val Lys Ile Ser Met Asp Ile Phe Val Arg Lys Phe Gln Pro Asp<br>315                   320              325 | 1133 |
| aga tat cag ctt tgg aaa caa gga aag gat ata tac acc att gat cac<br>Arg Tyr Gln Leu Trp Lys Gln Gly Lys Asp Ile Tyr Thr Ile Asp His<br>330                 335              340             345 | 1181 |
| acg aag cct act cca gca tcc acc cct gaa gta aaa gca tgg ctg cag<br>Thr Lys Pro Thr Pro Ala Ser Thr Pro Glu Val Lys Ala Trp Leu Gln | 1229 |

-continued

|     |     |     |     |     | 350 |     |     |     | 355 |     |     |     | 360 |     |     |      |
|-----|-----|-----|-----|-----|-----|-----|-----|-----|-----|-----|-----|-----|-----|-----|-----|------|
| agg | agg | agg | aaa | gta | aga | aaa | gca | tcc | cga | agc | ttc | cag | tgt | gct | agg | 1277 |
| Arg | Arg | Arg | Lys | Val | Arg | Lys | Ala | Ser | Arg | Ser | Phe | Gln | Cys | Ala | Arg |      |
|     |     |     | 365 |     |     |     | 370 |     |     |     | 375 |     |     |     |     |      |

| tct | acc | tct | aaa | agg | cct | aag | gct | gat | gag | gaa | gag | gaa | gtg | tca | gat | 1325 |
|-----|-----|-----|-----|-----|-----|-----|-----|-----|-----|-----|-----|-----|-----|-----|-----|------|
| Ser | Thr | Ser | Lys | Arg | Pro | Lys | Ala | Asp | Glu | Glu | Glu | Glu | Val | Ser | Asp |      |
|     |     |     | 380 |     |     |     | 385 |     |     |     | 390 |     |     |     |     |      |

| gaa | gtc | gat | ggg | gca | gag | gtc | cct | aac | ccc | gac | tca | gtc | aca | gat | gac | 1373 |
|-----|-----|-----|-----|-----|-----|-----|-----|-----|-----|-----|-----|-----|-----|-----|-----|------|
| Glu | Val | Asp | Gly | Ala | Glu | Val | Pro | Asn | Pro | Asp | Ser | Val | Thr | Asp | Asp |      |
|     |     | 395 |     |     |     | 400 |     |     |     | 405 |     |     |     |     |     |      |

| ctc | aag | gtc | agt | gaa | aag | tca | gaa | gca | gca | gtg | aag | ctg | agg | aac | aca | 1421 |
|-----|-----|-----|-----|-----|-----|-----|-----|-----|-----|-----|-----|-----|-----|-----|-----|------|
| Leu | Lys | Val | Ser | Glu | Lys | Ser | Glu | Ala | Ala | Val | Lys | Leu | Arg | Asn | Thr |      |
| 410 |     |     |     |     | 415 |     |     |     |     | 420 |     |     |     |     | 425 |      |

| gaa | gca | tct | tca | gaa | gaa | gag | tca | tct | gct | agc | agg | atg | cag | gtg | gag | 1469 |
|-----|-----|-----|-----|-----|-----|-----|-----|-----|-----|-----|-----|-----|-----|-----|-----|------|
| Glu | Ala | Ser | Ser | Glu | Glu | Glu | Ser | Ser | Ala | Ser | Arg | Met | Gln | Val | Glu |      |
|     |     |     |     | 430 |     |     |     |     | 435 |     |     |     |     | 440 |     |      |

| cag | aat | tta | tca | gat | cat | atc | aaa | ctc | tca | gga | aac | agc | tgc | tta | agt | 1517 |
|-----|-----|-----|-----|-----|-----|-----|-----|-----|-----|-----|-----|-----|-----|-----|-----|------|
| Gln | Asn | Leu | Ser | Asp | His | Ile | Lys | Leu | Ser | Gly | Asn | Ser | Cys | Leu | Ser |      |
|     |     |     |     | 445 |     |     |     |     | 450 |     |     |     |     | 455 |     |      |

| aca | tct | gta | aca | gaa | gac | ata | aaa | act | gag | gat | gac | aaa | gct | tat | gca | 1565 |
|-----|-----|-----|-----|-----|-----|-----|-----|-----|-----|-----|-----|-----|-----|-----|-----|------|
| Thr | Ser | Val | Thr | Glu | Asp | Ile | Lys | Thr | Glu | Asp | Asp | Lys | Ala | Tyr | Ala |      |
|     |     |     | 460 |     |     |     | 465 |     |     |     | 470 |     |     |     |     |      |

| tat | aga | agt | gta | cct | tct | ata | tcc | agt | gag | gct | gat | gat | tcc | att | cca | 1613 |
|-----|-----|-----|-----|-----|-----|-----|-----|-----|-----|-----|-----|-----|-----|-----|-----|------|
| Tyr | Arg | Ser | Val | Pro | Ser | Ile | Ser | Ser | Glu | Ala | Asp | Asp | Ser | Ile | Pro |      |
|     | 475 |     |     |     |     | 480 |     |     |     |     | 485 |     |     |     |     |      |

| ttg | tct | act | ggc | tat | gag | aag | ccc | gag | aaa | tca | gac | cca | tcc | gag | ctt | 1661 |
|-----|-----|-----|-----|-----|-----|-----|-----|-----|-----|-----|-----|-----|-----|-----|-----|------|
| Leu | Ser | Thr | Gly | Tyr | Glu | Lys | Pro | Glu | Lys | Ser | Asp | Pro | Ser | Glu | Leu |      |
| 490 |     |     |     |     | 495 |     |     |     |     | 500 |     |     |     |     | 505 |      |

| tca | tgg | cca | aag | tca | cct | gag | tca | tgc | tca | tca | gtg | gca | gag | agt | aat | 1709 |
|-----|-----|-----|-----|-----|-----|-----|-----|-----|-----|-----|-----|-----|-----|-----|-----|------|
| Ser | Trp | Pro | Lys | Ser | Pro | Glu | Ser | Cys | Ser | Ser | Val | Ala | Glu | Ser | Asn |      |
|     |     |     |     | 510 |     |     |     |     | 515 |     |     |     |     | 520 |     |      |

| ggt | gtg | tta | aca | gag | gga | gaa | gag | agt | gat | gtg | gag | agc | cat | ggg | aat | 1757 |
|-----|-----|-----|-----|-----|-----|-----|-----|-----|-----|-----|-----|-----|-----|-----|-----|------|
| Gly | Val | Leu | Thr | Glu | Gly | Glu | Glu | Ser | Asp | Val | Glu | Ser | His | Gly | Asn |      |
|     |     |     | 525 |     |     |     |     | 530 |     |     |     |     | 535 |     |     |      |

| ggc | ctt | gaa | cct | ggg | gaa | atc | cca | gcg | gtc | ccc | agt | gga | gag | aga | aat | 1805 |
|-----|-----|-----|-----|-----|-----|-----|-----|-----|-----|-----|-----|-----|-----|-----|-----|------|
| Gly | Leu | Glu | Pro | Gly | Glu | Ile | Pro | Ala | Val | Pro | Ser | Gly | Glu | Arg | Asn |      |
|     |     | 540 |     |     |     |     | 545 |     |     |     |     | 550 |     |     |     |      |

| agc | ttc | aaa | gtc | ccc | agt | ata | gca | gag | gga | gag | aac | aaa | acc | tct | aag | 1853 |
|-----|-----|-----|-----|-----|-----|-----|-----|-----|-----|-----|-----|-----|-----|-----|-----|------|
| Ser | Phe | Lys | Val | Pro | Ser | Ile | Ala | Glu | Gly | Glu | Asn | Lys | Thr | Ser | Lys |      |
| 555 |     |     |     |     | 560 |     |     |     |     | 565 |     |     |     |     |     |      |

| agt | tgg | cgc | cat | cca | ctt | agc | agg | cct | cca | gca | aga | tct | ccg | atg | act | 1901 |
|-----|-----|-----|-----|-----|-----|-----|-----|-----|-----|-----|-----|-----|-----|-----|-----|------|
| Ser | Trp | Arg | His | Pro | Leu | Ser | Arg | Pro | Pro | Ala | Arg | Ser | Pro | Met | Thr |      |
| 570 |     |     |     |     | 575 |     |     |     |     | 580 |     |     |     |     | 585 |      |

| ctt | gtg | aag | cag | cag | gcg | cca | agt | gat | gaa | gaa | ttg | cct | gag | gtt | ctg | 1949 |
|-----|-----|-----|-----|-----|-----|-----|-----|-----|-----|-----|-----|-----|-----|-----|-----|------|
| Leu | Val | Lys | Gln | Gln | Ala | Pro | Ser | Asp | Glu | Glu | Leu | Pro | Glu | Val | Leu |      |
|     |     |     |     | 590 |     |     |     |     | 595 |     |     |     |     | 600 |     |      |

| tcc | att | gag | gag | gaa | gtg | gaa | gaa | aca | gag | tct | tgg | gcg | aaa | cct | ctc | 1997 |
|-----|-----|-----|-----|-----|-----|-----|-----|-----|-----|-----|-----|-----|-----|-----|-----|------|
| Ser | Ile | Glu | Glu | Glu | Val | Glu | Glu | Thr | Glu | Ser | Trp | Ala | Lys | Pro | Leu |      |
|     |     |     | 605 |     |     |     |     | 610 |     |     |     |     | 615 |     |     |      |

| atc | cac | ctt | tgg | cag | acg | aag | tcc | cct | aac | ttc | gca | gct | gag | caa | gag | 2045 |
|-----|-----|-----|-----|-----|-----|-----|-----|-----|-----|-----|-----|-----|-----|-----|-----|------|
| Ile | His | Leu | Trp | Gln | Thr | Lys | Ser | Pro | Asn | Phe | Ala | Ala | Glu | Gln | Glu |      |
|     |     | 620 |     |     |     |     | 625 |     |     |     |     | 630 |     |     |     |      |

| tat | aat | gca | aca | gtg | gcc | agg | atg | aag | cca | cac | tgt | gcc | atc | tgc | act | 2093 |
|-----|-----|-----|-----|-----|-----|-----|-----|-----|-----|-----|-----|-----|-----|-----|-----|------|
| Tyr | Asn | Ala | Thr | Val | Ala | Arg | Met | Lys | Pro | His | Cys | Ala | Ile | Cys | Thr |      |
|     | 635 |     |     |     |     | 640 |     |     |     |     | 645 |     |     |     |     |      |

| ctg | ctc | atg | ccg | tac | cac | aag | cca | gat | agc | agc | aat | gaa | gaa | aat | gat | 2141 |
|-----|-----|-----|-----|-----|-----|-----|-----|-----|-----|-----|-----|-----|-----|-----|-----|------|
| Leu | Leu | Met | Pro | Tyr | His | Lys | Pro | Asp | Ser | Ser | Asn | Glu | Glu | Asn | Asp |      |
| 650 |     |     |     |     | 655 |     |     |     |     | 660 |     |     |     |     | 665 |      |

| gct | aga | tgg | gag | aca | aaa | tta | gat | gaa | gtc | gtt | aca | tcg | gag | gga | aag | 2189 |

```
Ala Arg Trp Glu Thr Lys Leu Asp Glu Val Val Thr Ser Glu Gly Lys
            670                 675                 680 act aag ccc ctc ata cca gag atg tgt ttt att tat agt gaa gaa aat    2237
Thr Lys Pro Leu Ile Pro Glu Met Cys Phe Ile Tyr Ser Glu Glu Asn
            685                 690                 695 ata gaa tat tct cca ccc aat gcc ttc ctt gaa gag gat gga aca agt    2285
Ile Glu Tyr Ser Pro Pro Asn Ala Phe Leu Glu Glu Asp Gly Thr Ser
        700                 705                 710 ctc ctt att tcc tgt gca aag tgc tgc gta cgg gtt cat gca agt tgt    2333
Leu Leu Ile Ser Cys Ala Lys Cys Cys Val Arg Val His Ala Ser Cys
        715                 720                 725 tat ggt att cct tct cat gag atc tgt gat gga tgg ctg tgt gcc cgg    2381
Tyr Gly Ile Pro Ser His Glu Ile Cys Asp Gly Trp Leu Cys Ala Arg
730                 735                 740                 745 tgc aaa aga aat gcg tgg aca gca gaa tgc tgt ctc tgc aat ttg aga    2429
Cys Lys Arg Asn Ala Trp Thr Ala Glu Cys Cys Leu Cys Asn Leu Arg
                750                 755                 760 gga ggt gct ctt aag caa acg aag aac aat agg tgg gcc cat gtc atg    2477
Gly Gly Ala Leu Lys Gln Thr Lys Asn Asn Arg Trp Ala His Val Met
            765                 770                 775 tgc gcc gtt gcg gtc cca gaa gtt cga ttc act aat gtc cca gaa agg    2525
Cys Ala Val Ala Val Pro Glu Val Arg Phe Thr Asn Val Pro Glu Arg
            780                 785                 790 aca caa ata gat gta ggc aga ata cct tta cag agg tta aaa ttg aaa    2573
Thr Gln Ile Asp Val Gly Arg Ile Pro Leu Gln Arg Leu Lys Leu Lys
        795                 800                 805 tgc atc ttc tgc aga cac cgg gtt aag agg gtc tct gga gcc tgc atc    2621
Cys Ile Phe Cys Arg His Arg Val Lys Arg Val Ser Gly Ala Cys Ile
810                 815                 820                 825 cag tgt tcc tac ggt cgc tgc ccg gcc tcc ttc cat gtc act tgt gcc    2669
Gln Cys Ser Tyr Gly Arg Cys Pro Ala Ser Phe His Val Thr Cys Ala
                830                 835                 840 cat gct gct ggg gta ctg atg gag cct gat gat tgg cct tat gtg gtg    2717
His Ala Ala Gly Val Leu Met Glu Pro Asp Asp Trp Pro Tyr Val Val
            845                 850                 855 aac att aca tgc ttt cga cat aag gtc aac ccc aac gtg aag tcc aag    2765
Asn Ile Thr Cys Phe Arg His Lys Val Asn Pro Asn Val Lys Ser Lys
            860                 865                 870 gct tgc gag aag gtc att tcc gtg ggt caa acg gtc atc acg aag cat    2813
Ala Cys Glu Lys Val Ile Ser Val Gly Gln Thr Val Ile Thr Lys His
        875                 880                 885 cgg aac acc cgg tat tac agt tgc aga gtg atg gct gtg aca tcg cag    2861
Arg Asn Thr Arg Tyr Tyr Ser Cys Arg Val Met Ala Val Thr Ser Gln
890                 895                 900                 905 acc ttc tat gag gtc atg ttt gat gat ggc tcc ttt agc aga gac aca    2909
Thr Phe Tyr Glu Val Met Phe Asp Asp Gly Ser Phe Ser Arg Asp Thr
                910                 915                 920 ttt cct gag gat atc gtg agc cga gac tgt ctg aag ctg ggc cca cct    2957
Phe Pro Glu Asp Ile Val Ser Arg Asp Cys Leu Lys Leu Gly Pro Pro
            925                 930                 935 gct gag gga gaa gtc gtc caa gtc aag tgg ccc gat ggc aaa ctc tat    3005
Ala Glu Gly Glu Val Val Gln Val Lys Trp Pro Asp Gly Lys Leu Tyr
            940                 945                 950 gga gca aaa tat ttt gga tca aat att gcc cac atg tac cag gtt gag    3053
Gly Ala Lys Tyr Phe Gly Ser Asn Ile Ala His Met Tyr Gln Val Glu
        955                 960                 965 ttt gaa gat gga tcc cag ata gca atg aag aga gag gac atc tac act    3101
Phe Glu Asp Gly Ser Gln Ile Ala Met Lys Arg Glu Asp Ile Tyr Thr
970                 975                 980                 985
```

-continued

```
tta gat gaa gag tta ccc aag aga gtg aaa gct cga ttt tcc aca gcc     3149
Leu Asp Glu Glu Leu Pro Lys Arg Val Lys Ala Arg Phe Ser Thr Ala
            990                 995                1000 tct gac atg cga ttt gaa gac acg ttt tat gga gca gac att atc         3194
Ser Asp Met Arg Phe Glu Asp Thr Phe Tyr Gly Ala Asp Ile Ile
        1005                1010                1015 caa ggg gag aga aag aga caa aga gtg ctg agc tcc agg ttt aag         3239
Gln Gly Glu Arg Lys Arg Gln Arg Val Leu Ser Ser Arg Phe Lys
    1020                1025                1030 aat gaa tat gtg gcc gac cct gta tac cgc act ttt ttg aag agc         3284
Asn Glu Tyr Val Ala Asp Pro Val Tyr Arg Thr Phe Leu Lys Ser
1035                1040                1045 tct ttc cag aag aag tgc cag aag aga cag       tagtctgcat acatcgctgc 3334
Ser Phe Gln Lys Lys Cys Gln Lys Arg Gln
            1050                1055
```
aggccacaga gcagcttggg ttggaaaaga aagatgaag ggacatcctt ggggctgtgc  3394
cgtgagattt gctggcatag gtgacagggt gtgtctctga cagtggtaaa tcgggtttcc  3454
agagtttggt caccaaaaat acaaaataca cacaatgaat tggacgcagc aatctgaaat  3514
catctctagt cttgctttca cttgtgagca gttgtcttct atgatcccaa agaagttttc  3574
taagtgaaag gaaatactag tgaatcaccc acaaggaaaa gccactgcca cagaggaggc  3634
gggtccccctt gtgcggctta gggccctgtc aggaaacaca cggggacctc tctctctagc  3694
tccagcaggt ggcacctcgg tacccagcgg gtagggcgat aatttatata ttttccacag  3754
tcagggaagg actctcactt atttgtttca aattgcagtt tttataaaac atttttaaaa  3814
cacaaatggc atgtatgcta atgagattta cccgtgtgct atctgtattt cccttgtaca  3874
gaacttttac attttttgaat attcctatta cttttgattg tgtctgatgg gaactgagtt  3934
gttggccttt gtgaaatgaa attttttggct cttgagaaag aattcttatg aattgttatg  3994
cgaatttttat atatttaaag agggagatct ggggctgtta tttttaaaca ctttttttca  4054
taatacatat tccgagtaga tatttataaa atatatgttt ctttcattat gtgtttgtaa  4114
aattagagtt taaataaata tgctttgatg catagttttg aactaatgta acatgatttt  4174
tcttttttaa aacagcctga aaatgtacta gtgtttaaaa ataaagattt ccattttctc  4234
caaaaaaaaa aaaaaaaaa                                                4253

<210> SEQ ID NO 3
<211> LENGTH: 1056
<212> TYPE: PRT
<213> ORGANISM: Homo sapiens

<400> SEQUENCE: 3

Met Glu Val Ala Glu Val Glu Ser Pro Leu Asn Pro Ser Cys Lys Ile
1               5                   10                  15

Met Thr Phe Arg Pro Ser Met Glu Glu Phe Arg Glu Phe Asn Lys Tyr
            20                  25                  30

Leu Ala Tyr Met Glu Ser Lys Gly Ala His Arg Ala Gly Leu Ala Lys
        35                  40                  45

Val Ile Pro Pro Lys Glu Trp Lys Pro Arg Gln Cys Tyr Asp Asp Ile
    50                  55                  60

Asp Asn Leu Leu Ile Pro Ala Pro Ile Gln Gln Met Val Thr Gly Gln
65                  70                  75                  80

Ser Gly Leu Phe Thr Gln Tyr Asn Ile Gln Lys Lys Ala Met Thr Val
                85                  90                  95

Lys Glu Phe Arg Gln Leu Ala Asn Ser Gly Lys Tyr Cys Thr Pro Arg

-continued

```
                100                 105                 110
Tyr Leu Asp Tyr Glu Asp Leu Glu Arg Lys Tyr Trp Lys Asn Leu Thr
            115                 120                 125

Phe Val Ala Pro Ile Tyr Gly Ala Asp Ile Asn Gly Ser Ile Tyr Asp
        130                 135                 140

Glu Gly Val Asp Glu Trp Asn Ile Ala Arg Ile Asn Thr Val Leu Asp
145                 150                 155                 160

Val Val Glu Glu Cys Gly Ile Ser Ile Glu Gly Val Asn Thr Pro
                165                 170                 175

Tyr Leu Tyr Phe Gly Met Trp Lys Thr Thr Phe Ala Trp His Thr Glu
            180                 185                 190

Asp Met Asp Leu Tyr Ser Ile Asn Tyr Leu His Phe Gly Glu Pro Lys
        195                 200                 205

Ser Trp Tyr Ala Ile Pro Pro Glu His Gly Lys Arg Leu Glu Arg Leu
    210                 215                 220

Ala Gln Gly Phe Phe Pro Ser Ser Gln Gly Cys Asp Ala Phe Leu
225                 230                 235                 240

Arg His Lys Met Thr Leu Ile Ser Pro Ser Val Leu Lys Lys Tyr Gly
                245                 250                 255

Ile Pro Phe Asp Lys Ile Thr Gln Glu Ala Gly Glu Phe Met Ile Thr
            260                 265                 270

Phe Pro Tyr Gly Tyr His Ala Gly Phe Asn His Gly Phe Asn Cys Ala
        275                 280                 285

Glu Ser Thr Asn Phe Ala Thr Val Arg Trp Ile Asp Tyr Gly Lys Val
    290                 295                 300

Ala Lys Leu Cys Thr Cys Arg Lys Asp Met Val Lys Ile Ser Met Asp
305                 310                 315                 320

Ile Phe Val Arg Lys Phe Gln Pro Asp Arg Tyr Gln Leu Trp Lys Gln
                325                 330                 335

Gly Lys Asp Ile Tyr Thr Ile Asp His Thr Lys Pro Thr Pro Ala Ser
            340                 345                 350

Thr Pro Glu Val Lys Ala Trp Leu Gln Arg Arg Arg Lys Val Arg Lys
        355                 360                 365

Ala Ser Arg Ser Phe Gln Cys Ala Arg Ser Thr Ser Lys Arg Pro Lys
    370                 375                 380

Ala Asp Glu Glu Glu Val Ser Asp Glu Val Asp Gly Ala Glu Val
385                 390                 395                 400

Pro Asn Pro Asp Ser Val Thr Asp Leu Lys Val Ser Glu Lys Ser
                405                 410                 415

Glu Ala Ala Val Lys Leu Arg Asn Thr Glu Ala Ser Ser Glu Glu Glu
            420                 425                 430

Ser Ser Ala Ser Arg Met Gln Val Glu Gln Asn Leu Ser Asp His Ile
        435                 440                 445

Lys Leu Ser Gly Asn Ser Cys Leu Ser Thr Ser Val Thr Glu Asp Ile
    450                 455                 460

Lys Thr Glu Asp Lys Ala Tyr Ala Tyr Arg Ser Val Pro Ser Ile
465                 470                 475                 480

Ser Ser Glu Ala Asp Asp Ser Ile Pro Leu Ser Thr Gly Tyr Glu Lys
                485                 490                 495

Pro Glu Lys Ser Asp Pro Ser Glu Leu Ser Trp Pro Lys Ser Pro Glu
            500                 505                 510

Ser Cys Ser Ser Val Ala Glu Ser Asn Gly Val Leu Thr Glu Gly Glu
        515                 520                 525
```

-continued

```
Glu Ser Asp Val Glu Ser His Gly Asn Gly Leu Glu Pro Gly Glu Ile
    530                 535                 540
Pro Ala Val Pro Ser Gly Glu Arg Asn Ser Phe Lys Val Pro Ser Ile
545                 550                 555                 560
Ala Glu Gly Glu Asn Lys Thr Ser Lys Ser Trp Arg His Pro Leu Ser
                565                 570                 575
Arg Pro Pro Ala Arg Ser Pro Met Thr Leu Val Lys Gln Gln Ala Pro
            580                 585                 590
Ser Asp Glu Glu Leu Pro Glu Val Leu Ser Ile Glu Glu Val Glu
        595                 600                 605
Glu Thr Glu Ser Trp Ala Lys Pro Leu Ile His Leu Trp Gln Thr Lys
    610                 615                 620
Ser Pro Asn Phe Ala Ala Glu Gln Glu Tyr Asn Ala Thr Val Ala Arg
625                 630                 635                 640
Met Lys Pro His Cys Ala Ile Cys Thr Leu Leu Met Pro Tyr His Lys
                645                 650                 655
Pro Asp Ser Ser Asn Glu Glu Asn Asp Ala Arg Trp Glu Thr Lys Leu
            660                 665                 670
Asp Glu Val Val Thr Ser Glu Gly Lys Thr Lys Pro Leu Ile Pro Glu
        675                 680                 685
Met Cys Phe Ile Tyr Ser Glu Glu Asn Ile Glu Tyr Ser Pro Pro Asn
    690                 695                 700
Ala Phe Leu Glu Glu Asp Gly Thr Ser Leu Leu Ile Ser Cys Ala Lys
705                 710                 715                 720
Cys Cys Val Arg Val His Ala Ser Cys Tyr Gly Ile Pro Ser His Glu
                725                 730                 735
Ile Cys Asp Gly Trp Leu Cys Ala Arg Cys Lys Arg Asn Ala Trp Thr
            740                 745                 750
Ala Glu Cys Cys Leu Cys Asn Leu Arg Gly Gly Ala Leu Lys Gln Thr
        755                 760                 765
Lys Asn Asn Arg Trp Ala His Val Met Cys Ala Val Ala Val Pro Glu
    770                 775                 780
Val Arg Phe Thr Asn Val Pro Glu Arg Thr Gln Ile Asp Val Gly Arg
785                 790                 795                 800
Ile Pro Leu Gln Arg Leu Lys Leu Lys Cys Ile Phe Cys Arg His Arg
                805                 810                 815
Val Lys Arg Val Ser Gly Ala Cys Ile Gln Cys Ser Tyr Gly Arg Cys
            820                 825                 830
Pro Ala Ser Phe His Val Thr Cys Ala His Ala Ala Gly Val Leu Met
        835                 840                 845
Glu Pro Asp Asp Trp Pro Tyr Val Val Asn Ile Thr Cys Phe Arg His
    850                 855                 860
Lys Val Asn Pro Asn Val Lys Ser Lys Ala Cys Glu Lys Val Ile Ser
865                 870                 875                 880
Val Gly Gln Thr Val Ile Thr Lys His Arg Asn Thr Arg Tyr Tyr Ser
                885                 890                 895
Cys Arg Val Met Ala Val Thr Ser Gln Thr Phe Tyr Glu Val Met Phe
            900                 905                 910
Asp Asp Gly Ser Phe Ser Arg Asp Thr Phe Pro Glu Asp Ile Val Ser
        915                 920                 925
Arg Asp Cys Leu Lys Leu Gly Pro Pro Ala Glu Gly Glu Val Val Gln
    930                 935                 940
```

Val Lys Trp Pro Asp Gly Lys Leu Tyr Gly Ala Lys Tyr Phe Gly Ser
945                 950                 955                 960

Asn Ile Ala His Met Tyr Gln Val Glu Phe Glu Asp Gly Ser Gln Ile
            965                 970                 975

Ala Met Lys Arg Glu Asp Ile Tyr Thr Leu Glu Glu Leu Pro Lys
        980                 985                 990

Arg Val Lys Ala Arg Phe Ser Thr Ala Ser Asp Met Arg Phe Glu Asp
        995                 1000                1005

Thr Phe Tyr Gly Ala Asp Ile Ile Gln Gly Glu Arg Lys Arg Gln
    1010                1015                1020

Arg Val Leu Ser Ser Arg Phe Lys Asn Glu Tyr Val Ala Asp Pro
    1025                1030                1035

Val Tyr Arg Thr Phe Leu Lys Ser Ser Phe Gln Lys Lys Cys Gln
    1040                1045                1050

Lys Arg Gln
    1055

<210> SEQ ID NO 4
<211> LENGTH: 24
<212> TYPE: DNA
<213> ORGANISM: Artificial
<220> FEATURE:
<223> OTHER INFORMATION: Primer 2484

<400> SEQUENCE: 4
aggagtgagc caccgcaccc agcc                                        24

<210> SEQ ID NO 5
<211> LENGTH: 35
<212> TYPE: DNA
<213> ORGANISM: Artificial
<220> FEATURE:
<223> OTHER INFORMATION: Primer PDJ34

<400> SEQUENCE: 5
tgagcyrwga tyryrccayt gcactccagc ctggg                            35

<210> SEQ ID NO 6
<211> LENGTH: 19
<212> TYPE: DNA
<213> ORGANISM: Artificial
<220> FEATURE:
<223> OTHER INFORMATION: Primer W1f

<400> SEQUENCE: 6
cgggttaaga gggtctctg                                              19

<210> SEQ ID NO 7
<211> LENGTH: 20
<212> TYPE: DNA
<213> ORGANISM: Artificial
<220> FEATURE:
<223> OTHER INFORMATION: Primer W1r

<400> SEQUENCE: 7
ggatgtccct tcatcttctc                                             20

<210> SEQ ID NO 8
<211> LENGTH: 22
<212> TYPE: DNA
<213> ORGANISM: Artificial
<220> FEATURE:
<223> OTHER INFORMATION: Primer W2f

```
<400> SEQUENCE: 8
aataccttgc atacatggag tc                                          22

<210> SEQ ID NO 9
<211> LENGTH: 22
<212> TYPE: DNA
<213> ORGANISM: Artificial
<220> FEATURE:
<223> OTHER INFORMATION: Primer W2r

<400> SEQUENCE: 9
cttcttcaac cacatccaag ac                                          22

<210> SEQ ID NO 10
<211> LENGTH: 5
<212> TYPE: DNA
<213> ORGANISM: Homo sapiens

<400> SEQUENCE: 10 aataa                                                              5
```